United States Patent [19]
Ali et al.

[11] Patent Number: 6,069,143
[45] Date of Patent: May 30, 2000

[54] FIBRINOGEN RECEPTOR ANTAGONISTS

[75] Inventors: Fadia El-Fehail Ali, Cherry Hill, N.J.; William Edward Bondinell, Wayne, Pa.; Raul Rolando Calvo, Royersford, Pa.; Thomas Wen-Fu Ku, Dresher, Pa.; William Henry Miller, Schwenksville, Pa.; James Samanen, Phoenixville, Pa.; Joseph Walter Venslavsky, Wayne, Pa.; Tobias Oregon Yellin, Villanova, Pa.

[73] Assignee: SmithKline Beecham Corporation, Philadelphia, Pa.

[21] Appl. No.: 08/584,030

[22] Filed: Jan. 11, 1996

Related U.S. Application Data

[63] Continuation-in-part of application No. 08/359,799, Dec. 20, 1994, abandoned.

[51] Int. Cl.[7] ...... A61K 31/495; A61K 31/445; C07D 401/12; C07D 401/14
[52] U.S. Cl. ...... 514/252; 514/255; 514/316; 514/318; 544/357; 544/360; 544/364; 544/393; 546/189; 546/194
[58] Field of Search ...... 544/360; 514/252, 514/316; 546/189

[56] References Cited

U.S. PATENT DOCUMENTS

| | | | |
|---|---|---|---|
| 5,700,801 | 12/1997 | Pieper et al. | 514/252 |
| 5,756,519 | 5/1998 | Bondinell et al. | 514/316 |
| 5,786,371 | 7/1998 | Tsaklakidis et al. | 514/318 |
| 5,814,636 | 9/1998 | Katano et al. | 514/252 |

FOREIGN PATENT DOCUMENTS

| | | |
|---|---|---|
| 42 41 632 | 6/1994 | Germany . |
| 94/22835 | 10/1994 | WIPO . |

OTHER PUBLICATIONS

Himmelsbach et al, *Chemical Abstracts*, vol. 121 No. 133976, (Abstract for DE 4241632), 1994.

Pieper et al, *Chemical Abstracts*, vol. 125, No. 195688 (Abstract for WO 96 20173, Jul. 4, 1996).

*Primary Examiner*—Emily Bernhardt
*Attorney, Agent, or Firm*—Mary E. McCarthy; Stephen Venetianer; Charles M. Kinzig

[57] ABSTRACT

This invention relates to compounds of the formula:

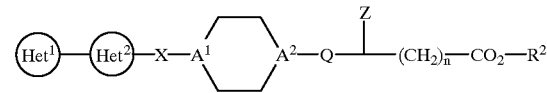

which are effective for inhibiting platelet aggregation, pharmaceutical compositions for effecting such activity, and a method for inhibiting platelet aggregation.

6 Claims, No Drawings

FIBRINOGEN RECEPTOR ANTAGONISTS

This is a continuation-in-part of application Ser. No. 08/359,799, filed on Dec. 20, 1994 now abandoned.

FIELD OF THE INVENTION

This invention relates to novel compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g., inhibitors of the GPIIb-IIIa protein) which have potent in vivo and in vitro effects and lack the peptide backbone structure of amino acid sequences.

The present invention discloses novel compounds. These compounds inhibit the GPIIb-IIIa receptor and inhibit platelet aggregation.

SUMMARY OF THE INVENTION

In one aspect this invention is a compound as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

DETAILED DESCRIPTION OF THE INVENTION

This invention discloses compounds which inhibit platelet aggregation. The compounds of the instant invention are believed to interact favorably with the GPIIb-IIIa receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

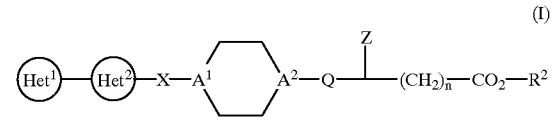

wherein:

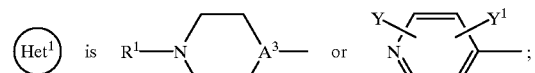

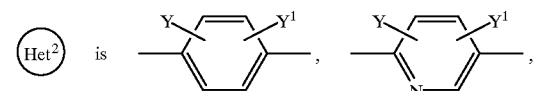

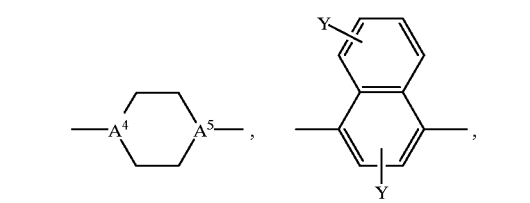

or a (6,5), (6,6), or (6,7) bicyclic heterocycle;

$R^1$ is a hydrogen, $C_{1-6}$alkyl, $(CH)_n$aryl, $C_{1-6}$alkylOC(O)—, HC≡C—CH$_2$—,

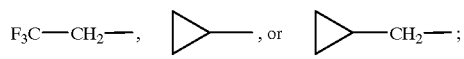

$A^1$, $A^3$, $A^4$, and $A^5$ independently are N or CH, with the proviso that $A^3$ and $A^4$ are not simultaneously N;

$A^2$ is CH, C(OH), or N;

Y and $Y^1$ independently are hydrogen, halogen, $C_{1-6}$alkyl, $C(R^2)_3$, $N(R^2)_2$, $C(R^2)_2OR^2CH_2CHOR^2$, $CF_3$, —$(CH_2)_n$-phenyl, or —NC(O)—$(CH_2)_n$—B;

B is

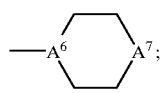

$A^6$ is CH or N;

$A^7$ is $NR^4$ or CH $R^4$;

X is a colvalent bond, $C(O)N(R^2)_2$, $N(R^2)_2C(O)$, $SO_2N(R^2)_2$, $N(R^2)_2SO_2$, $C(O)$, $C(R^2)_2$, S, O, $-(CH_2)_n-N(R^3)_2$, $C(R^2)_2OR^2$, $C(O)C(R^2)_2$, $C(S)N(R^2)_2$, $N(R^2)_2C(S)$, $C(R^2)_2C(O)$, $C(R^2)_2C(R^2)_2$, $CHOHC(R^2)_2$, $C(R^2)_2CHOH$, or $C(R^2)=C(R^2)$;

Q is a single bond or C(O);

Z is hydrogen, $C_{1-4}$alkyl, $OR^2$, $CH_2OR^2$, $CH_2COR^2$, $CHCON(R^2)_2CO_2R^2$, $CON(R^2)_2$, $-CH=C-$, $-C\equiv C-$, $COR^2$, or $-(CH_2)_n$-aryl;

each aryl is

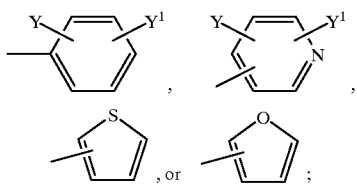

each $R^2$ independently is H or $C_{1-6}$alkyl;

$R^3$ is H, $C_{1-6}$alkyl, or $C(O)C_{1-6}$alkyl;

$R^4$ is H, $C_{1-6}$alkyl, or $(CH_2)_m-CO_2R^2$;

each n independently is 0–3; and m is 1 or 2;

or a pharmaceutically acceptable salt thereof.

More specifically, the compounds of this invention are compounds of formula (Ia):

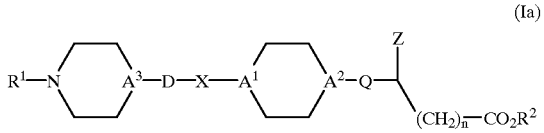

wherein:

$R^1$ is hydrogen, $C_{1-6}$alkyl, $HC\equiv C-CH_2-$, $F_3C-CH_2-$, $C_{1-6}$alkylOC(O),

D is

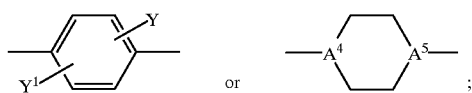

$A^1$, $A^3$, $A^4$, and $A^5$ independently are N or CH, with the proviso that $A^3$ and $A^4$ are not simultaneously N;

$A^2$ is CH, C(OH), or N;

Y and $Y^1$ independently are hydrogen, $C_{1-6}$alkyl, halogen, $CF_3$, or $-(CH_2)_n$-phenyl;

X is $C(O)NR^2$, $NR^2C(O)$, $SO_2NR^2$, $NR^2SO_2$, $C(O)$, $C(R^2)_2$, S, O, $-(CH_2)_n-N(R^3)_2$, $CR^2OR^2$, $C(O)C(R^2)_2$, $C(R^2)_2C(O)$, $CH_2CH_2$, $CHOHCH_2$, $CH_2CHOH$, $CR^2=CR^2$, $C(S)N(R^2)_2$, or $N(R^2)_2C(S)$;

Q is a single bond or C(O);

Z is hydrogen, $C_{1-4}$alkyl, $OR^2$, $CH_2OR^2$, $CH_2CO_2R^2$, $CH_2CONR^2R^2$, $CO_2R^2$, $CONR^2R^2$, $-CH=CH-$, $-C\equiv C-$, $COR^2$, or $-(CH_2)_n$-phenyl;

each n independently is 0–3;

each $R^2$ independently is H or $C_{1-6}$alkyl; and $R^3$ is H, $C_{1-6}$alkyl, or $C(O)C_{1-6}$alkyl;

or a pharmaceutically acceptable salt thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which the compounds have unsaturated double bonds, both the cis (Z) and trans (E) are within the scope of this invention. The meaning of any substituent at any one occurrence is independent of its meaning, or any other substituent's meaning, at any other occurrence, unless specified otherwise.

With reference to formula (Ia), compounds of formula (II) are preferred:

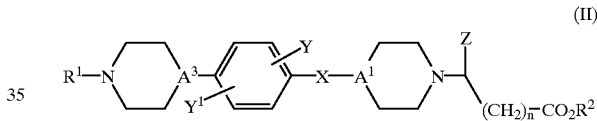

wherein:

$R^1$ is hydrogen, or $C_{1-6}$alkyl;

$A^1$ and $A^3$ independently are N or CH;

Y and $Y^1$ independently are hydrogen, $C_{1-6}$alkyl, halogen, or $CF_3$;

X is $C(O)NR^2$, $NR^2C(O)$, $SO_2NR^2$, $NR^2SO_2$, $C(O)$, $C(R^2)_2$, S, O, $-(CH_2)_n-N(R^3)_2$, $C(S)N(R^2)_2$, or $N(R^2)_2C(S)$;

Z is hydrogen, $C_{1-4}$alkyl, $OR^2$, $CH_2OR^2$, $CH_2CO_2R^2$, or $CO_2R^2$;

each n independently is 0 or 1; and each $R^2$ independently is H or $C_{1-6}$alkyl;

or a pharmaceutically acceptable salt thereof.

Preferably, the compounds of formula (II) are those wherein $A^3$ is N, $A^1$ is CH, X is $C(O)NR^2$ or $NR^2C(O)$, Z is hydrogen, $R^1$ is hydrogen or $C_{1-4}$alkyl, and $R^2$ is hydrogen or $C_{1-4}$alkyl.

Specific embodiments of this invention are:

4-[[[4-(1-piperazinyl)phenyl]amino]carbonyl]-1-piperidineacetic acid;

methyl 4-[[[4-(1-piperazinyl)phenyl]amino]carbonyl]-1-piperidine acetate;

ethyl 4-[[[4-(1-piperazinyl)phenyl]amino]carbonyl]-1-piperidine acetate;

4-[[[4-(1-N-ethyloxycarbonyl-4-piperazinyl)phenyl]amino]carbonyl]-1-piperidine-methyl acetate;

4-[[[4-(1-N-ethyloxycarbonyl-4-piperazinyl)phenyl]amino]carbonyl]-1-piperidineacetic acid;

4-[[[4-(4-methyl-1-piperazinyl)phenyl]amino]carbonyl]-1-piperidineacetic acid;

4-[[[4-[4-(phenylmethyl)-1-piperazinyl]phenyl]carbonyl]amino]-1-piperidineacetic acid;

4-[[[4-(4-piperidinyl)phenyl]amino]carbonyl]-1-piperidineacetic acid;

4-[[[4-(4-pyridinyl)phenyl]amino]carbonyl]-1-piperidineacetic acid;

4-[[5-[2-(1-piperazinyl)pyridinyl]amino]carbonyl]-1-piperdineacetic acid;

4-[[[4-(1-piperazinyl)-3-chlorophenyl]amino]carbonyl]-1-piperdineacetic acid;

4-[[[4-(1-piperazinyl)naphth-1-yl]amino]carbonyl]-1-piperidineacetic acid;

4-[[[4-(1-piperazinyl)-3-(trifluoromethyl)phenyl]amino]carbonyl]-1-piperidineacetic acid;

4-[[[4-(1-piperazinyl)-2-(trifluoromethyl)phenyl]amino]carbonyl]-1-piperidineacetic acid;

4-[N-(4,4'-bipiperidinyl)amino]carbonyl-1-piperidineacetic acid;

4-[4-(1-piperazinyl)benzimidazol-2-yl]-1-piperidineacetic acid;

N,N'-[4-(1-piperazinyl)-1,2-phenylene]bis-[1-(carboxymethyl)-4-piperidinecarboxamide]tetrakis (trifluoroacetate);

4-[[[4-(1-piperazinyl)phenyl]methylamino]carbonyl]-1-piperidineacetic acid;

4-[[[(1-piperizinyl)phenyl]carbonyl]amino]-1-piperidineacetic acid;

4-[N-[4-(1-piperazinyl)benzyl]-N-acetyl]amino-1-piperidineacetic acid;

4-[[[4-(1-piperazinyl)phenyl]amino]thiocarbonyl]-1-piperidineacetic acid;

4-[[4-(1-piperazinyl)benzyl]amino]-1-piperidineacetic acid;

1-[[[4-(1-piperazinyl)phenyl]amino]carbonyl]-4-piperazineacetic acid;

1-[[[4-(1-piperazinyl)phenyl]amino]carbonyl]-4-piperidine acetic acid;

trans-4-[[[4-(1-piperazinyl)phenyl]amino]carbonyl-1-hydroxy-1-cyclohexaneacetic acid;

cis-4-[[[4-(1-piperazinyl)phenyl]amino]carbonyl]-1-hydroxy-1-cyciohexaneacetic acid;

4-[[[4-piperazinyl)phenyl]amino]carbonyl]-1-cyclohexanylacetic acid; or

4-[[[4-(1-piperazinyl)phenyl]amino]carbonyl]-1-piperidinepropionic acid;

or a pharmaceutically accetable salt thereof.

A preferred compound of this invention is 4-[[[4-(1-piperazinyl)phenyl]-amino]carbonyl]-1-piperidineacetic acid or a pharmaceutically acceptable salt thereof.

In the above description, $C_{1-4}$alkyl is meant to include methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof.

In the above desciption, a (6,5)-membered bicyclic heterocycle is meant to include any six-membered ring fused to any five-membered ring. Representative bicyclic rings formed by the combination of the six- and five-membered rings are: indene, isoindene, benzofuran, isobenzofuran, benzothiophene, isobenzothiophene, indole, indolenine, isobenzazole, 1,5-pyrindine, isoindazole, indoxazine, benzoxazole, anthranil, benzothiazole, and purine. Phenyl is a preferred six-membered ring, and imidazole and pyrrole are preferred five-membered rings. Thus, the preferred bicyclic rings formed by the combination of the six- and five-membered rings are benzimidazole and indole.

In the above desciption, a (6,6)-membered bicyclic heterocycle is meant to include any six-membered ring fused to any six-membered ring. Representative bicyclic rings formed by the combination of the six- and six-membered rings are: tetralin, quinoline, dihydroquinoline, tetrahydroquinoline, isoquinoline, dihydroisoquinoline, tetrahydroisoquinoline, quinazoline, dihydroquinazoline, tetrahydroquinazoline, 3,4-dihydro-2H-1,4-benzoxazine, and 3,4-dihydro-2-H-1,4-benzothiazine. Phenyl is a preferred six-membered ring, and piperidine is the second prefered six-membered ring, which is fused to said phenyl ring. Thus the preferred ring system is the 1,2,3,4-tetrahydroisoquinoline system.

In the above desciption, a (6,7)-membered bicyclic heterocycle is meant to include any six-membered ring fused to any seven-membered ring. Representative bicyclic rings formed by the combination of the six and seven-membered rings are: 1,2-benzo-1-cycloheptene, 1,2-benzo-1,3-cycloheptadiene and 1,2-benzo-1,4-cycloheptadiene compounds; 1-, 2- and 3-benzazepine, dihydrobenzazepine and tetrahydrobenzazepine compounds; 1,2-, 1,3-, 1,4-, 1,5-, 2,3- and 2,4-benzodiazepine, dihydrobenzodiazepine and tetrahdyrobenzodiazepine compounds, 1,2-, 1,3-, 1,4-, 1,5-, 2,1-, 2,3-, 2,4-, 2,5-, 3,1-, 3,2-, and 4,1-benzoxazepine, dihydrobenzoxazepine and tetrabenzoxazepine compounds; 1,2-, 1,3-, 1,4-, 1,5-, 2,1-, 2,3-, 2,5-, 3,1-, 3,2- and 4,1-benzothiazepine, dihydrobenzothiazepine and tetrahydrobenzothiazepine compounds; and other similar saturated and unsatruated stable pyridazepine, pyrazazepine, pyridazin-azepine, pyrimidinazepine, mono- and di-oxo- (e.g., sulfoxyl, sulfonyl) benzothiazepine, benzodioxepin and benzoxathiepin compounds. Phenyl is a preferred six-membered ring, and di- or tetrahydroazepine, diazepine, thiazepine and oxazepine are preferred seven-membered rings. Particularly, preferred ring systems are the benzazepine and benzodiazepine systems.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-6}$alkyl, Nph refers to 1- or 2-naphthyl and cHex refers to cyclohexyl. MeArg is $N^\alpha$-methyl arginine. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to N-ethyl-N'(dimethylaminopropyl)-carbodiimide. HOBt refers to 1-hydroxybenzotriazole, THF refers to tetrahydrofuran, DMF refers to dimethyl formamide, NBS refers to N-bromosuccinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (III) with a compound of the formula (IV):

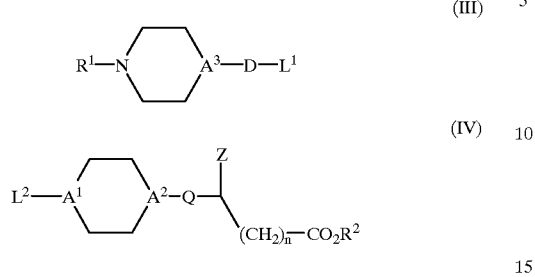

wherein $A^1$, $A^2$, $A^3$, D, $R^1$, $R^2$, Q, Z, and n are as defined in formula (I), with any reactive functional groups protected; and $L^1$ and $L^2$ are functional groups which are capable of reacting to form the X linkage;

and thereafter removing any protecting groups, and optionally forming a pharmaceutically acceptable salt.

It will be apparent that the precise identity of $L^1$ and $L^2$ will be dependent upon the the linkage being formed. General methods for preparing the linkage are described, for example, in EP-A 0 372 486 and EP-A 0 381 033 and EP-A 0 478 363, which are incorporated herein by reference.

For instance, if X is CONH, $L^1$ may be —$NH_2$ and $L^2$ may be OH (as in an acid) or Cl (as in an acid chloride). When $L^2$ is OH, a coupling agent is used.

Similarly, if X is NHCO, $L^1$ may be —$CO_2H$ or CO—Cl and $L^2$ may be —$NH_2$.

Where X is $NHSO_2$, $L^1$ may be $SO_2Cl$ and $L^2$ may be —$NH_2$. Where X is $SO_2NH$, $L^1$ may be —$NH_2$ and $L^2$ may be $SO_2Cl$. Methods to prepare such sulfonyl chlorides are disclosed, for instance, in *J. Org. Chem.*, 23, 1257 (1958).

If X is CH=CH, $L^1$ may be —CHO and $L^2$ may be CH=P—$Ph_3$. Alternately, $L^1$ may be CH=P—$Ph_3$ and $L^2$ may be CHO.

Where X is $CH_2CH_2$ may be obtained by reduction of a suitably protected compound wherein X is CH=CH.

Where X is C≡C, $L^1$ may be —C≡CH and $L^2$ may be —Br. Alternately, when X is C≡C, $L^1$ may be Br, I or $CF_3SO_3$ and $L^2$ may be C≡CH and the coupling may be catalyzed by palladium and a base.

Where X is $C(O)CH_2$, $L^1$ may be $C(O)CH_2Br$ and $L^2$ may be hydrogen on a nitrogen of a piperazine ring.

Compounds wherein X is $CHOHCH_2$ may be prepared from a suitably protected compound where X is CH=CH by the procedure disclosed in *J. Org. Chem.*, 54, 1354 (1989).

Compounds wherein X is $CH_2CHOH$ may be obtained from a suitably protected compound where X is CH=CH by hydroboration and basic oxidation as disclosed in *Tet. Lett.*, 31, 231 (1990).

Scheme I

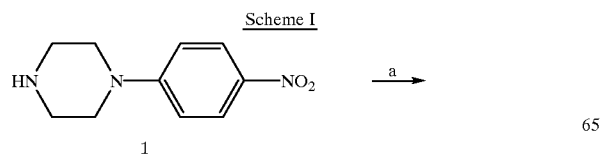

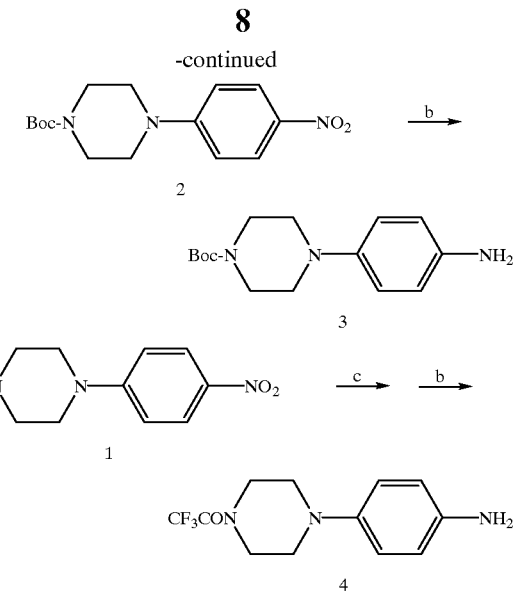

a) BocO, $CH_2Cl_2$;
b) H, Pd/C, EtOH;
c) $CF_3CO_2O$, $Et_3N$, $CH_2Cl_2$

Scheme I provides a method to prepare certain precursors to be employed in the preparation of compounds described by Formula (1), where $Het^1$ is a piperidine or piperazine and $Het^2$ is is an aryl group. Accordingly, the terminal secondary nitrogen in a piperazinylnitroaryl compound is protected with an appropriate acyl-type protecting group and the nitro group is reduced to a primary amine to give compounds such as 3 or 4.

Scheme II

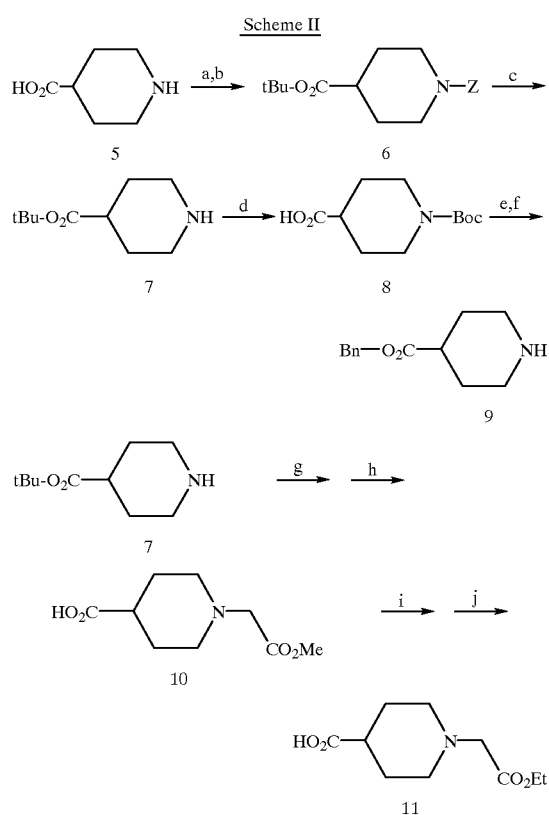

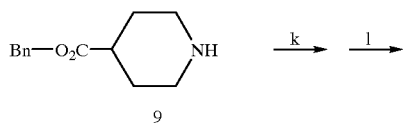

9

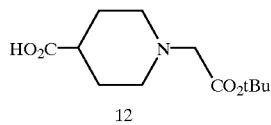

12

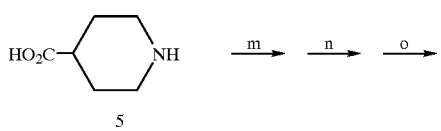

5

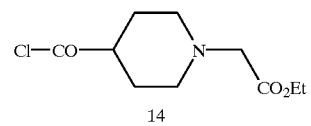

14 a) SOCl$_2$, CH$_2$Cl$_2$;
b) SOCl$_2$, CH$_2$Cl$_2$

Scheme III provides a method to prepare the acid halides of the precursors in Scheme 2 to be employed in the preparation of compounds described by Formula (1), where A$^1$ is CH and A$^2$ is N, and Q is a single bond.

Scheme IVa

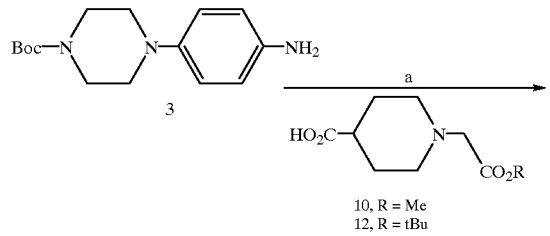

10, R = Me
12, R = tBu

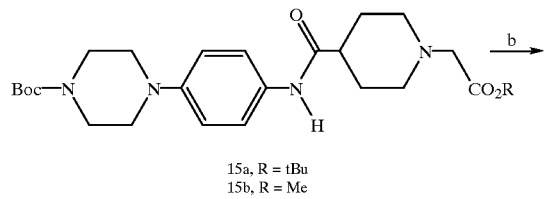

15a, R = tBu
15b, R = Me

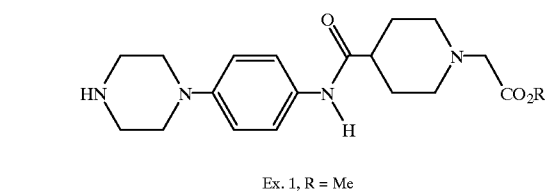

Ex. 1, R = Me
Ex. 2, R = H a) R = tBu: HBTU, Et$_3$N, DMF;
R = Me: DCC/HOBt, Et$_3$N, DMF;
b) TFA, CH$_2$Cl$_2$ a) CbzCl, 5N NaOH, THF/H$_2$O;
b) PhSO$_2$Cl, tBuOH, Pyr;
c) H$_2$, Pearlman's catalyst AcOH;
d) Boc$_2$O, CH$_3$CN;
e) Bn—Br, Et$_3$N/DMF;
f) TFA, CH$_2$Cl$_2$;
g) ClCH$_2$CO$_2$Me, Et$_3$N/CH$_3$CN;
h) TFA, CH$_2$Cl$_2$;
i) Cl—CH$_2$CO$_2$Et, Et$_3$N/CH$_3$CN;
j) TFA, CH$_2$Cl$_2$;
k) Cl—CH$_2$CO$_2$tBu, Et$_3$N/CH$_3$CN;
l) H$_2$/Pd—C, MeOH:
m) HCl/MeOH;
n) ClCH$_2$CO$_2$tBu, K$_2$CO$_3$,
1 N NaOH, H$_2$O
DIEA/acetone;

Scheme II provides a method to prepare certain other precursors to be employed in the preparation of compounds described by Formula (1), where A$^1$ is CH and A$^2$ is N, and Q is a single bond. Accordingly, the t-butyl ester of a piperidinyl-4-carboxylic acid, such as compound 7, is prepared from the Cbz-protected derivative, such as compound 6, while the benzyl ester, such as compound 9, is prepared from the Boc-protected derivative, such as compound 8. Such esters are then alkylated with haloacetic acid esters to give, after deprotection of the 4-carboxylicacid ester, 4-carboxy-piperidineacetate esters, such as compounds 10–12.

Scheme III

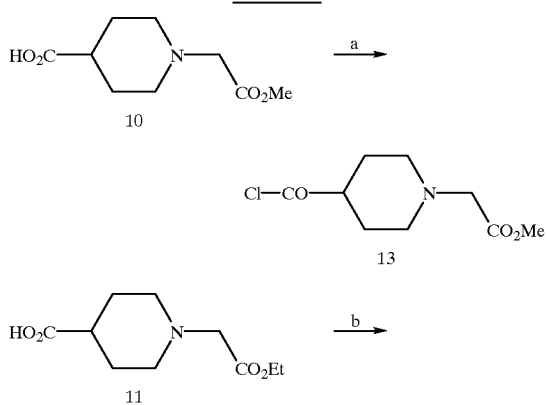

Scheme IVa provides a method for the preparation of compounds described by Formula (1), where Het$^1$ is a piperazine and Het$^2$ is an aryl group, X is an amide group, A$^1$ is CH and A$^2$ is N, and Q is a single bond. Accordingly, a 4-acylpiperazinylaniline (prepared via Scheme 1) is condensed with a 4-carboxypiperidineacetic acid ester (prepared via Scheme II) via methods employed in the art. Removal of both the amine and carboxyl protecting groups by standard conditions, for example when R$^4$=Boc and R$^2$=t-butyl in Formula (1), provides the desired compound as exemplified by the compound of Example 1.

Scheme IVb

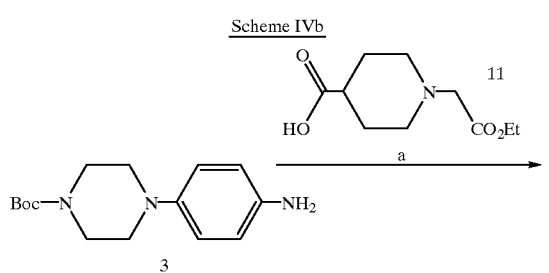

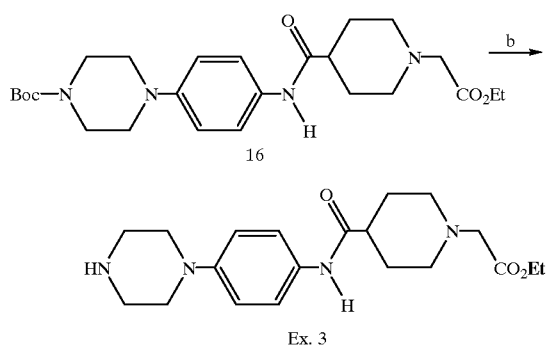

a) EDC/HOBt, Et₃N, DMF;
b) 4M HCl, dioxane, CH₂Cl₂

Scheme IVa and IVb also provide a method for the preparation of ester derivatives of compounds described by Formula (1), where Het¹ is a piperazine and Het² is is an aryl group, X is an amide group, $A^1$ is CH and $A^2$ is N, and Q is a single bond. Accordingly, removal of only the amine protecting group from the protected product amide, as exemplified by compound 15b in Scheme IVa and compound 16 in Scheme IVb, affords the title compounds of Example 2 and 3.

Scheme V

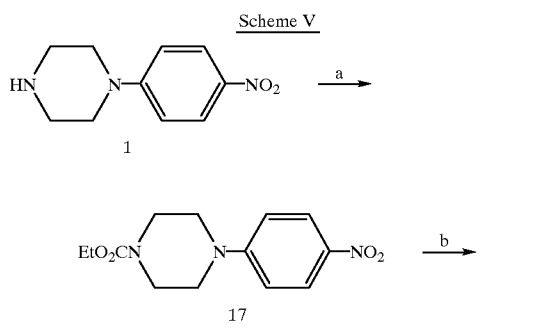

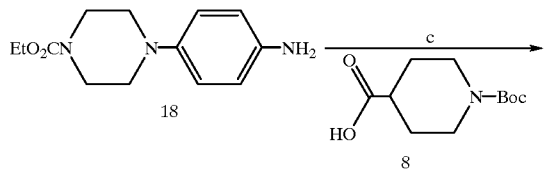

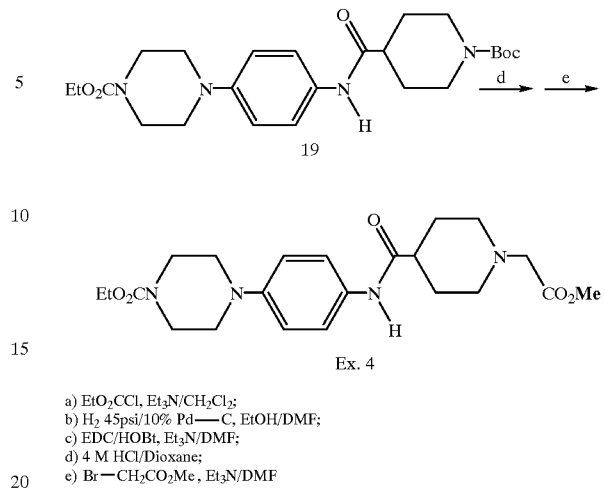

a) EtO₂CCl, Et₃N/CH₂Cl₂;
b) H₂ 45psi/10% Pd—C, EtOH/DMF;
c) EDC/HOBt, Et₃N/DMF;
d) 4 M HCl/Dioxane;
e) Br—CH₂CO₂Me, Et₃N/DMF Scheme V provides a method for preparing N-alkoxycarbonyl ester derivatives of compounds described by Formula (1), where Het1 is a piperazine and Het² is is an aryl group, X is an amide group, $A^1$ is CH and $A^2$ is N, and Q is a single bond. Accordingly, N-alkoxycarbonyl derivatives of piperazinylnitroaryl compounds, such as compound 1, are prepared by treating compounds, such as compound 1, with an alkylchloroformate, the nitro group is reduced by catalytic reduction to a primary amine, and acylated with an N-protected piperidine-4-carboyxlic acid, such as compound 8. The N-protecting group is removed by methods known in the art, and aklylated with a haloalkylcarboxylic acid ester, such as methylbromoacetate to give compounds such as the title compound of Example 4.

Scheme VI

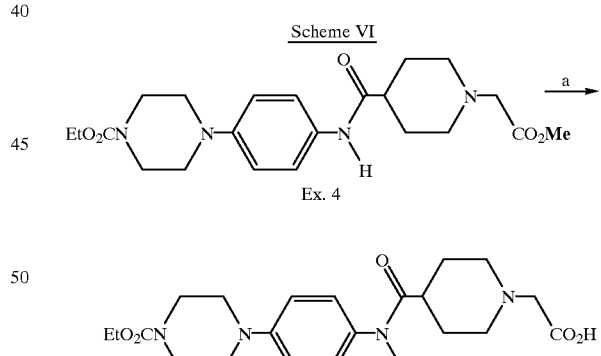

a) 1N NaOH, MeOH/THF

Scheme VI provides a method for preparing N-alkoxycarbonyl acid derivatives of compounds described by Formula (1), where Het¹ is a piperazine and Het² is is an aryl group, X is an amide group, $A^1$ is CH and $A^2$ is N, and Q is a single bond. Accordingly, the esters described in Scheme 5 are saponified by methods known in the art to give compounds such as the title compound of Example 5.

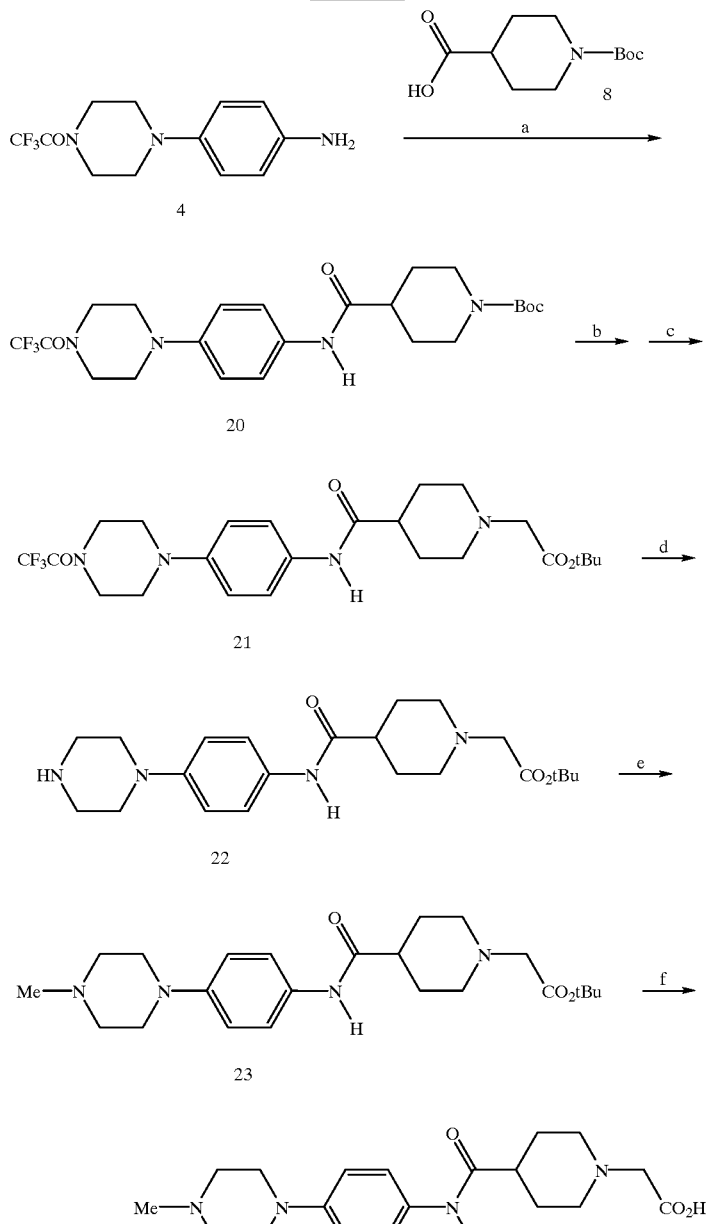

a) EDC/HOBt, Et₃N, DMF;
b) 4 M HCl/Dioxane;
c) Br—CH₂CO₂tBu, Et₃N/DMF;
d) 1N NaOH, MeOH/THF;
e) 77% aq. CH₂O, H₂ 35psi/10% Pd-C;
f) TFA/CH₂Cl₂

Scheme VII provides a method for preparing N-alkyl derivatives of compounds described by Formula (1), where $Het^1$ is a piperazine and $Het^2$ is is an aryl group, X is an amide group, $A^1$ is CH and $A^2$ is N, and Q is a single bond. Accordingly, a N-protected piperazinylaniline, such as 4 (prepared in Scheme I) is condensed with N-protected piperidine-4-carboxylic acid (prepared in Scheme II) by methods known in the art. The piperidinyl protecting group is removed standard conditions to allow for alkylation with an ester of a haloacetic acid, to give a compound such as 21. Removal of the N-piperazinyl protecting group allows then for alkylation, e.g. reductive alkylation with an aldehyde and an appropriate reducing agent to give. after saponification, N-alkyl-piperazines, such as the title compound of Example 6.

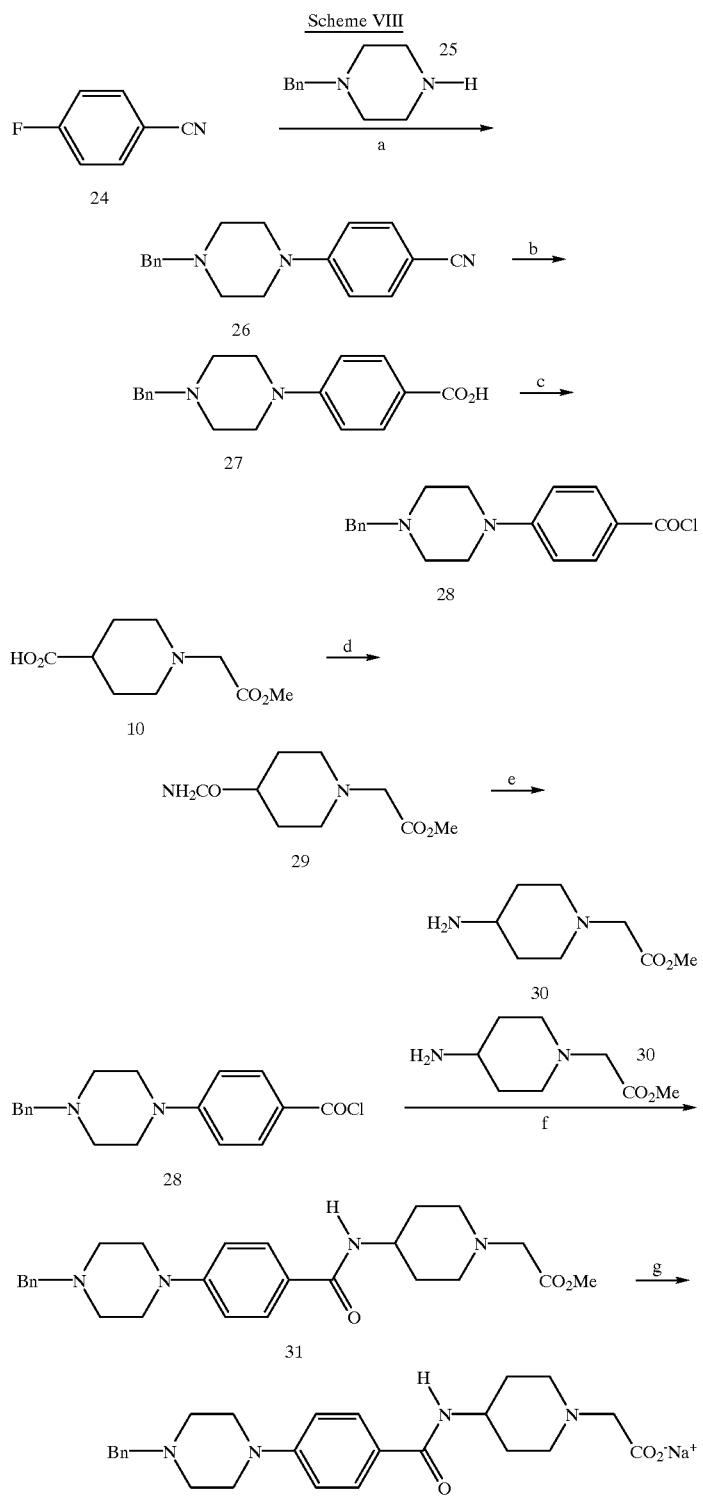
Scheme VIII
Ex. 7
a) heat, 48 h;
b) 50% NaOH;
c) SOCl$_2$, CH$_2$Cl$_2$;
d) DCC/HOBt/NH$_2$(g), DMF;
e) DPPA;
f) Et$_3$N, CH$_2$Cl$_2$;
g) 1N NaOH, MeOH/acetone Scheme VIII provides an alternate method from Scheme VII for preparing N-alkyl derivatives of compounds described by Formula (1), where Het1 is a pipeazine or piperazine and Het² is an aryl group, X is an amide group in the reverse sense of compounds prepared in Scheme VII, A¹ is CH and A² is N, and Q is a single bond. Accordingly, a mono-alkylpiperazine is treated with a 4-cyanoarylfluoride to give an alkylpiperazinylarylcyanide, such as compound 26. Under aqueous alkaline conditions the corresponding arylcarboxylic acid may be obtained. The acid halide of such a compound is condensed with a 4-aminopiperidinylacetic acid ester, such as 30 employing standard acylation conditions to give, after saponification of the ester product, compounds such as the title compound of Example 7. The intermediate compounds such as 30 may be obtained from the corresponding 4-carboxypiperdinylacetic acid esters (prepared in Scheme II) by Curtius rearrangement of the primary amide, such as 29.

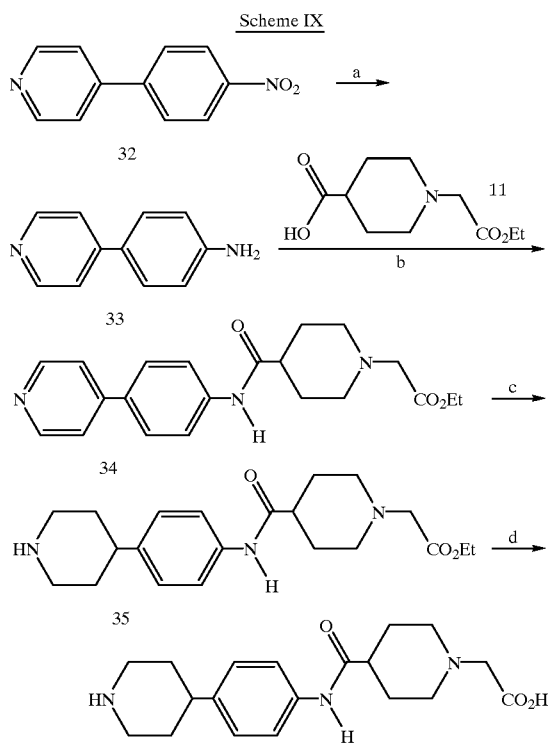

a) H₂ 50 psi/10% Pd-C, DMF;
b) EDC/HOBt, DIEA, DMF;
c) H₂ 47 psi/PtO₂, HCl, MeOH;
d) 1N NaOH, EtOH/THF Scheme IX provides a method for preparing 4-piperidinylaryl-4-amidopiperidineacetic acids described by Formula (1), where Het¹ is piperazine and Het² is is an aryl group, X is an amide group, A¹ is CH and A² is N, and Q is a single bond. Accordingly, a 4-pyridinoaniline, such as compound 33, is obtained by catalytic reduction of the corresponding nitroaryl compound. The aniline is condensed with a 4-carboxypiperidinylacetic acid ester (prepared in Scheme II) employing a standard set of acylation conditions to give a pyridinylarylamide, such as compound 34. Catalytic reduction of such a pyridine affords the corresponding piperidine, which is saponified to give compounds such as the title compound of Example 8.

a) EDC/HOBt, DIEA, DMF;
b) TFA, CH₂Cl₂

Scheme X provides a method for preparing 4-pyridinylaryl-4-amidopiperidineacetic acids described by Formula (1), where Het¹ is pyridine and Het² is is an aryl group, X is an amide group, A¹ is CH and A² is N, and Q is a single bond. Accordingly, a 4-pyridinylaniline, such as compound 33 is condensed with the relevant 4-carboxypiperidine acetic acid ester (prepared in Scheme II), employing methods known in the art, followed by deesterification to give compounds such as the title compound of Example 9.

-continued

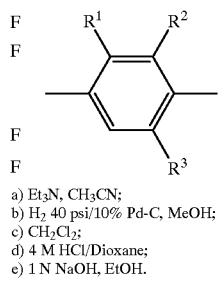

b. Ex.11: $R^1$ = Cl, $R^2$ = H, $R^3$ = H
c. Ex. 12:
   $R^1, R^2$ =—CH=CH—CH=CH—,
   $R^3$ = H
d. Ex. 13: $R^1$ = $CF_3$, $R^2$ = H, $R^3$ = H
e. Ex. 14: $R^1$ = H, $R^2$ = H, $R^3$ = $CF_3$ a) $Et_3N$, $CH_3CN$;
b) $H_2$ 40 psi/10% Pd-C, MeOH;
c) $CH_2Cl_2$;
d) 4 M HCl/Dioxane;
e) 1 N NaOH, EtOH.

Scheme XI provides a method for preparing 4-piperazinyl{aryl and heteroaryl}-4-amidopiperidineacetic acids described by Formula (1), where $Het^1$ is piperazine and $Het^2$ is is an aryl or heteroaryl group, X is an amide group, $A^1$ is CH and $A^2$ is N, and Q is a single bond. Accordingly, an N-protected-4-nitroarylpiperazine, such as compound 39, is obtained by arylation of an N-protected piperidine with the appropriate 4-nitro{aryl or heteroaryl}halide, such as compound 38. Catalytic reduction of the nitro compound gives the corresponding aniline, which is condensed with an acylhalide derivative of 4-carboxypiperidine acetic acid ester (prepared in Scheme III), such as compound 8. Protecting group removal by methods known in the art affords the desired compounds, as exemplified by the title compounds of Examples 10 and 11.

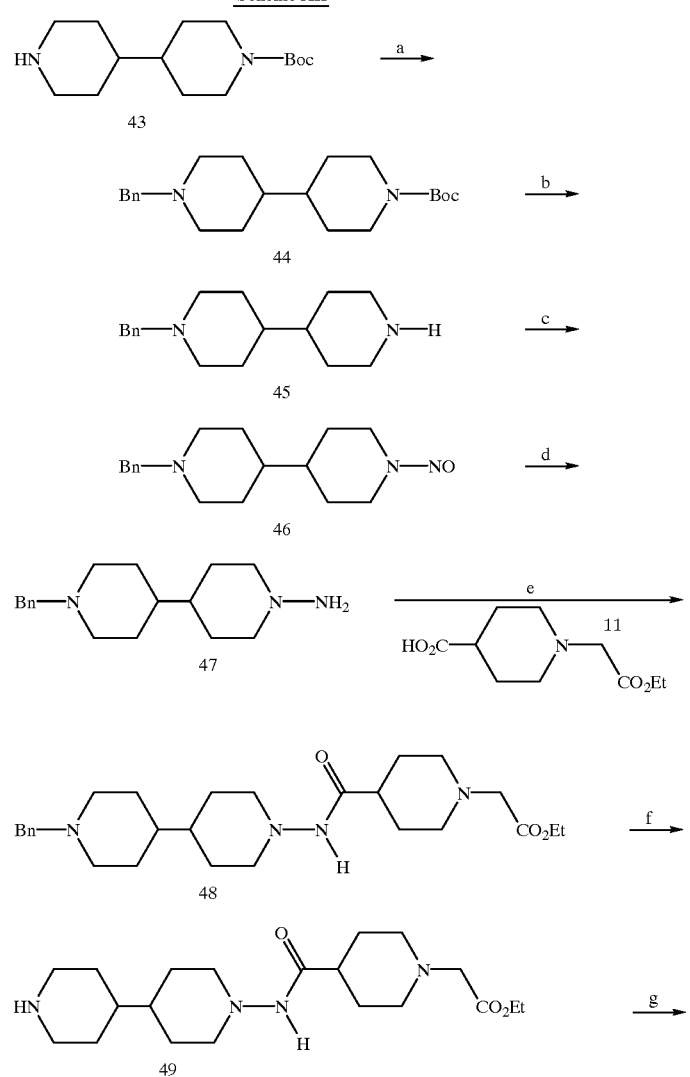

Scheme XII

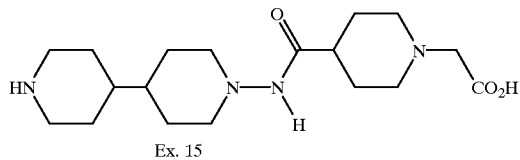

Ex. 15 a) BnBr, Et$_3$N, DMF;
b) 4M HCl/dioxane, CH$_2$Cl$_2$;
c) KNO$_2$, HCl/HOAc;
d) LiAlH$_4$, THF;
e) EDC/HOBt, DIEA, DMF;
f) H$_2$ 50 psi/Pearlman's catalyst, EtOH;
g) 1N NaOH, EtOH Scheme XII provides a method for preparing 4-[N-4,4'-(bipiperidinyl)aminocarbonyl-1-piperidineacetic acids described by Formula (1), where Het$^1$ is a piperidine and Het$^2$ is is a piperidine, X is an amide group, A$^1$ is CH and A$^2$ is N, and Q is a single bond. Accordingly, a mono-N-benzylbipiperidine, such as compound 45, is prepared by alkylation of a mono-N-protected-bipiperidine, followed by N-protecting group removal. The corresponding N-nitroso compound, such as compound 46, obtained for example by treating the amine with potassium nitrite in a mixture of concentrated hydrochloric and acetic acid, is reduced to the hydrazine, such as compound 47, with an agent such as LiAlH$_4$. Condensation with a 4-carboxypiperidine acetic acid ester (prepared in Scheme II) by methods known in the art affords, after protecting group removal, monoacylhydrazines such as the title compound in Example 15.

Scheme XIII

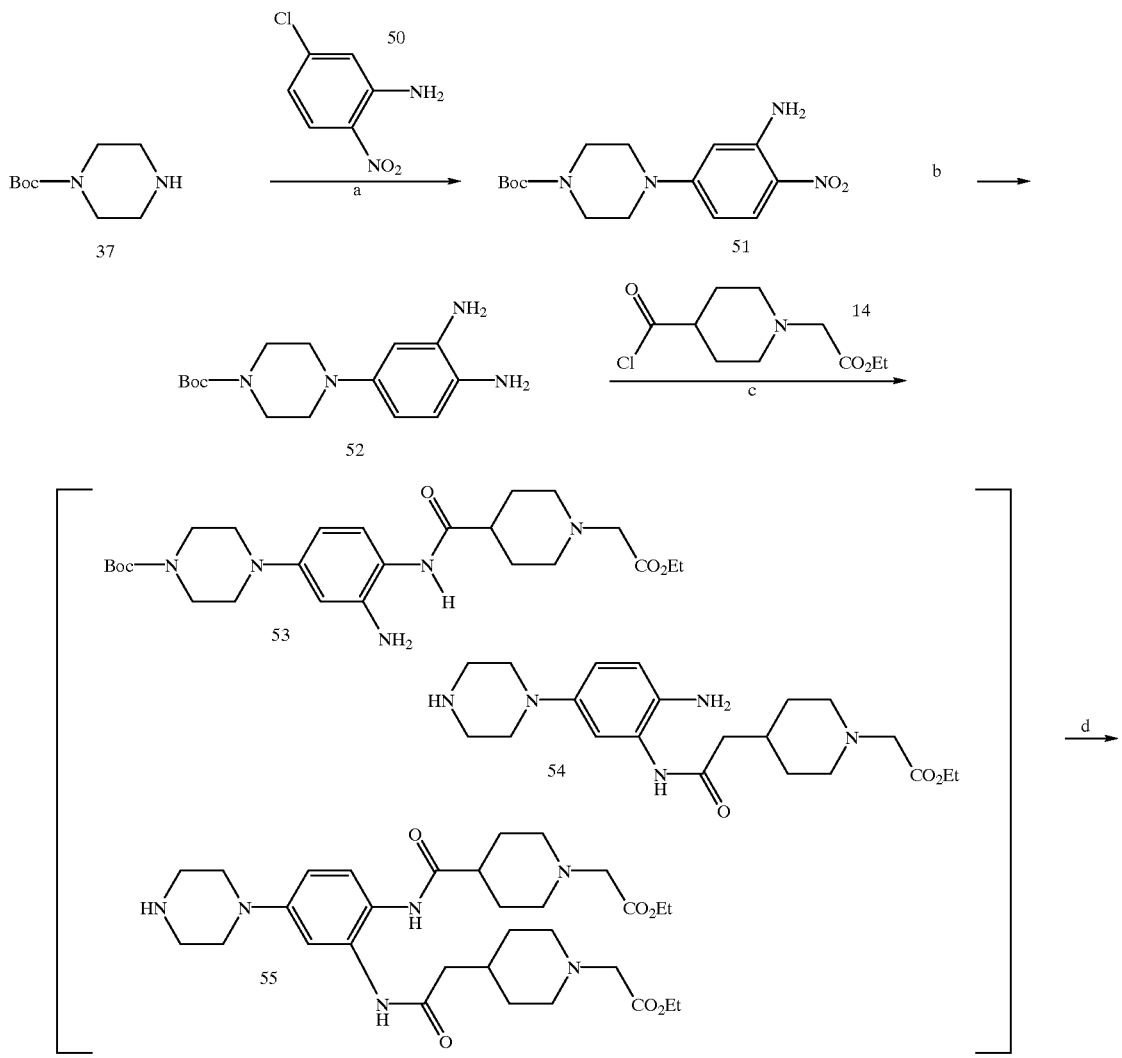

-continued

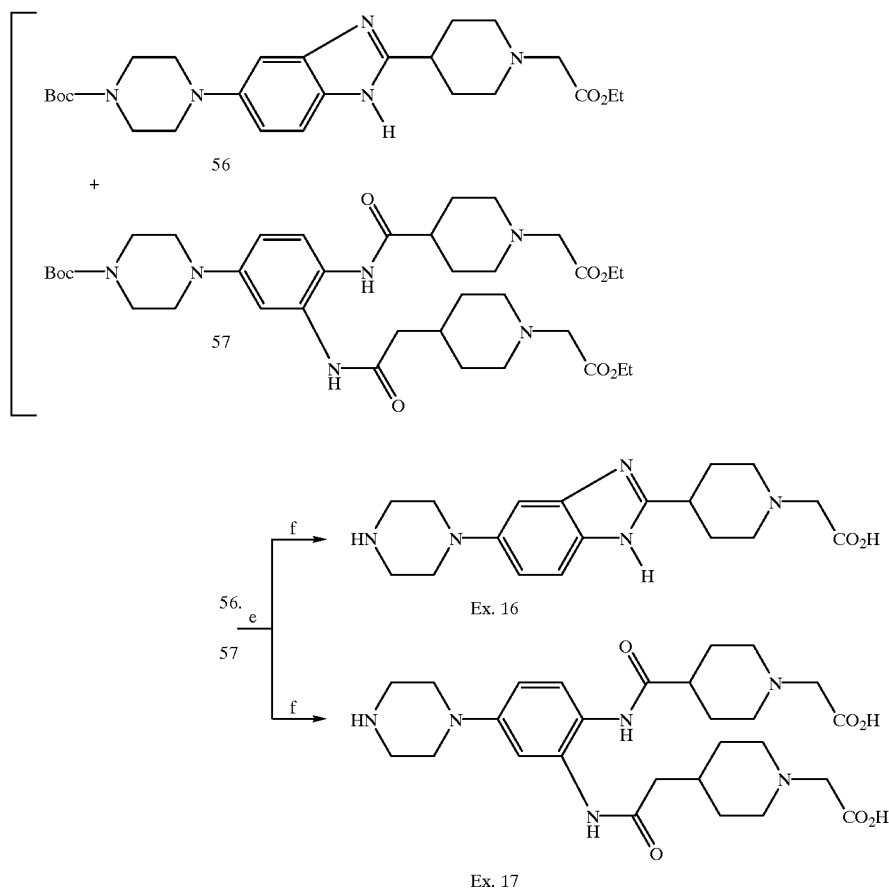

a) 1,4-DABCO, DMSO;
b) H₂ 40 psi/10% Pd-C, MeOH;
c) DIEA, CH₂Cl₂;
d) gl. AcOH;
e) TFA, CH₂Cl₂;
f) 1 N NaOH, MeOH/H₂O semi-prep hplc Scheme XIII provides a method for preparing 4-pipeazinylheteroaryl-4-amidopiperidineacetic acids described by Formula (1), where Het[1] is piperazine and Het[2] is is a bicyclic heteroaryl group, X is a covalent bond, $A^1$ is CH and $A^2$ is N, and Q is a single bond. Accordingly, a 4-piperazinylaryl-1,2-diamine bearing a piperazinyl protecting group, such as compound 52, is obtained by arylation of an N-protected piperidine with a 5-chloro-2-nitroaniline, such as 50, and catalytic reduction of the nitrogroup. Acylation with an acylhalide derivative of a 4-carboxypiperidine acetic acid ester (prepared in Scheme III) gives a mixture of mono- and di-acyl compounds, such as 53–55, which is heated in the presence of glacial acetic acid to give the protected desired bicyclic compound, such as 56. Protecting group removal, followed by semi-preparative chromatography affords the desired bicyclic compound, such as the title compound of Example 16.

Scheme XIII also provides a method for preparing pipeazinylaryl-3,4-bis(amidopiperidineacetic acids) described by Formula (1), where Het[1] is piperazine and Het[2] is is an aryl group, X is a covalent bond, m=2, $A^1$ is CH and $A^2$ is N, and Q is a single bond. Accordingly, the semi-preparative chromatography of deprotected product also affords the desired pipeazinylaryl-3,4-bis (amidopiperidineacetic acid), such as the title compound of Example 17.

Scheme XIV

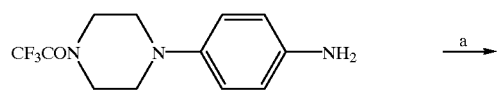

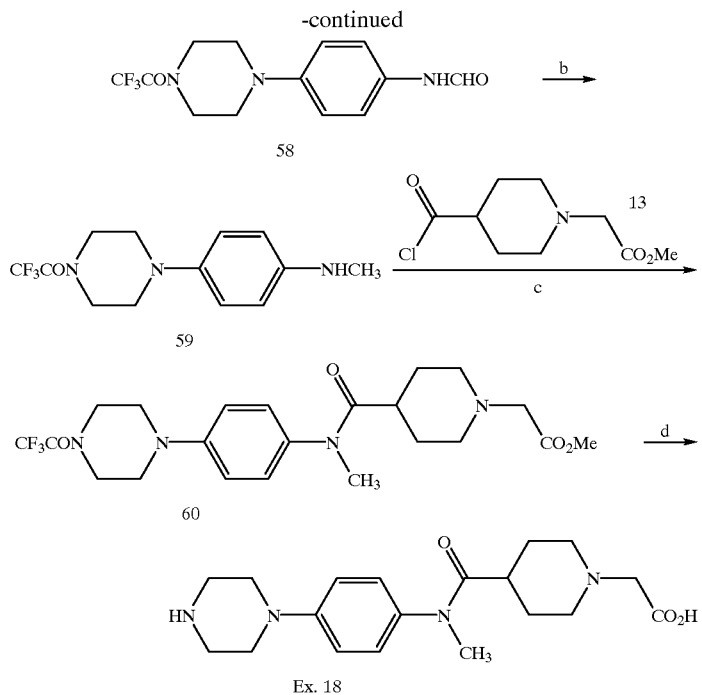

a) EtOCHO;
b) BH$_3$·Me$_2$S, THF;
c) Et$_3$N, CH$_2$Cl$_2$;
d) 1N NaOH, MeOH/THF

Scheme XIV provides a method for preparing 4-piperazinylaryl-4-alkylamidopiperidineacetic acids described by Formula (1), where Het$^1$ is piperazine and Het$^2$ is is an aryl group, X is an alkylamide group, A$^1$ is CH and A$^2$ is N, and Q is a single bond. Accordingly, the appropriate N-piperazine-protected, 4-N-alkylaminoarylpiperazine, such as compound 59, is obtained by reduction of the formyl derivative of an aniline, such as compound 4. Acylation with an acylhalide derivative of a 4-carboxypiperidine acetic acid ester (prepared in Scheme III), followed protecting group removal affords the N-alkylamides, such as the title compound of Example 18.

Scheme XV provides a method for preparing 4-piperaziny-aryl-4-amidopiperidineacetic acids described by Formula (1), where Het$^1$ is piperazine and Het$^2$ is is an aryl group, X is an amide group in the reverse sense of the compounds obtained in Scheme 1, A$^1$ is CH and A$^2$ is N, and Q is a single bond. Accordingly, the N-alkyl group in the product obtained from Scheme VIII, where N-alkyl is N-benzyl, is removed by catalytic hydrogenation, to afford compounds such as the title compound of Example 19.

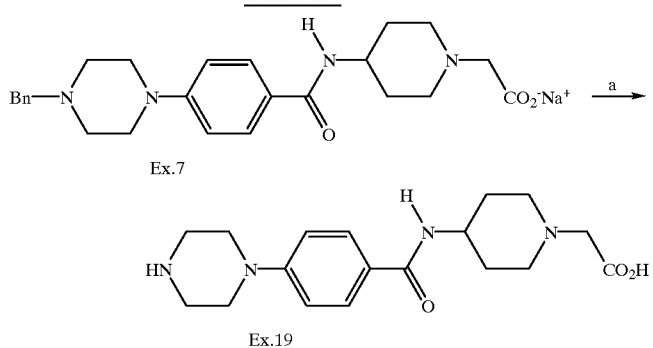

a) H$_2$ 50 psi/10% Pd-C, MeOH

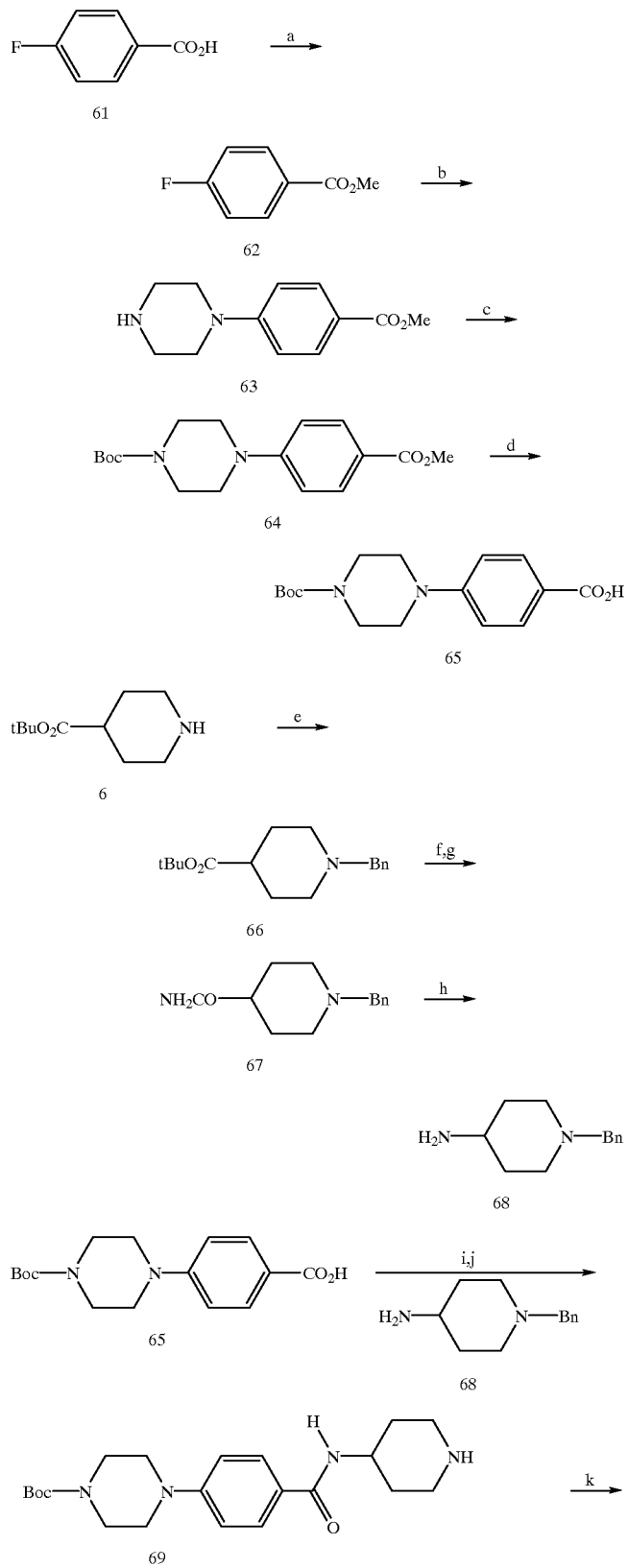

-continued

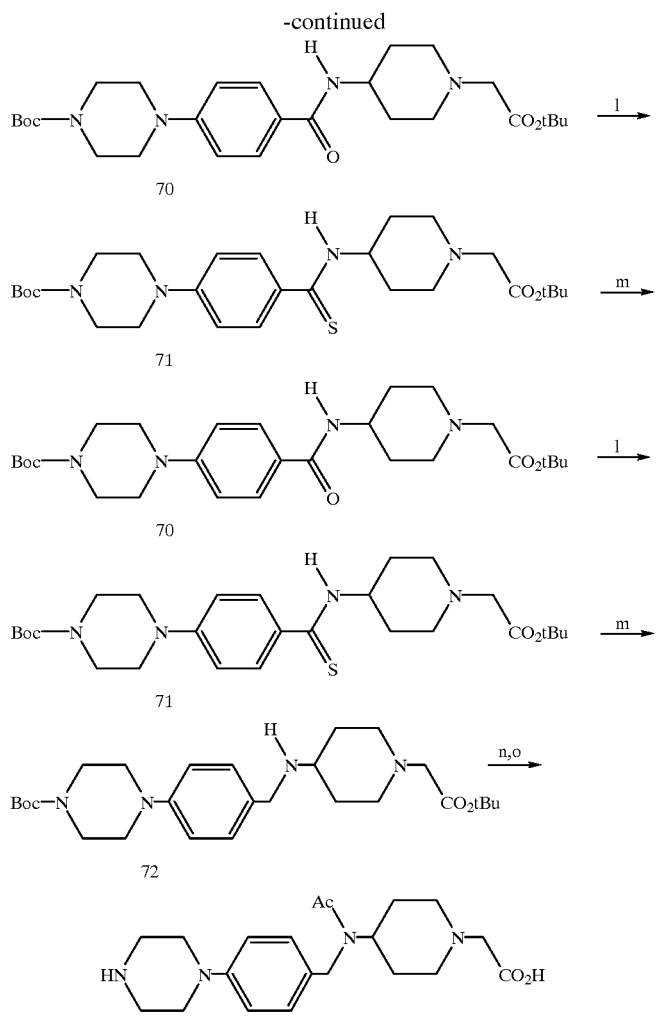

Ex. 20 a) SOCl₂, MeOH;
b) Piperazine, DMSO;
c) Boc₂O, CH₃CN;
d) 1N NaOH, MeOH/THF;
e) BnBr, Et₃N/DMF;
f) TFA;
g) EDC/HOBt/NH₃
(g)h) DPPA, DMF;
i) DCC/HOBt, DMF/Et₃N;
j) H₂, Pearlman's catalyst, MeOH:
k) Br—CH₂CO₂tBu, Et₃N/DMF;
l) Lawesson Reagent, toluene;
m) NaBH₄/NiCl₂.6H2O, THF/MeOH;
n) 1. Ac—Cl, Et₃N/CH₂Cl₂;
o) TFA/CH₂Cl₂

Scheme XVI provides a method for preparing 4-piperazinylaryl-4-methyl(N-acyl)amino-piperidineacetic acids described by Formula (1), where Het¹ is piperazine and Het² is is an aryl group, X is an N-alkyl-N-acylamino group, A¹ is CH and A² is N, and Q is a single bond. Accordingly, a piperazine undergoes arylation upon heating with a 4-fluorobenzoic acid ester. The resulting arylpiperazine is protected with a standard N-protecting group and saponified to the corresponding benzoic acid, such as compound 65. The benzoic acid is condensed with a piperazinyl-N-protected-4-aminopiperidine, such as compound 68, to give the corresponding amide. Removal of the piperidine protecting group, and alkylation with a haloacetic acid ester affords a compound such as 70.

The 4-aminopiperidines, such as 68, are obtained by Curtius rearrangement of the appropriate N-protected piperidine-4-carboxylic acid amide, derived from N-protection of a piperidine-4-carboxylic acid ester, such as compound 6.

The thioamide of a compound, such as 71, that is obtained by treating the amide, such as 74 with the Lawesson reagent, is reduced to the alkylamine, such as 72, via nickel-catalyzed hydroboration. Acylation, followed by protecting group removal affords the desired compound, exemplified by the title compound of Example 20.

Scheme XVII

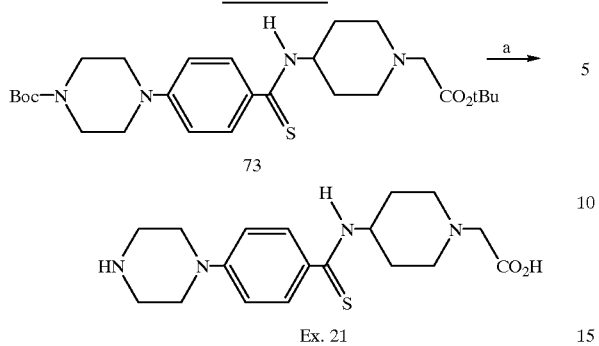

a) TFA, CH$_2$Cl$_2$

Scheme XVII provides a method for preparing 4-piperazinylaryl-4-thioamido-piperidineacetic acids described by Formula (1), where Het$^1$ is piperazine and Het$^2$ is is an aryl group, X is an thioamide group, A$^1$ is CH and A$^2$ is N, and Q is a single bond. Accordingly, the protecting groups on the thioamides, such as 3, described in Scheme XVI, are removed by methods known in the art to give the desired thioamides, as exemplified by the title compound of Example 21.

Scheme XVIII

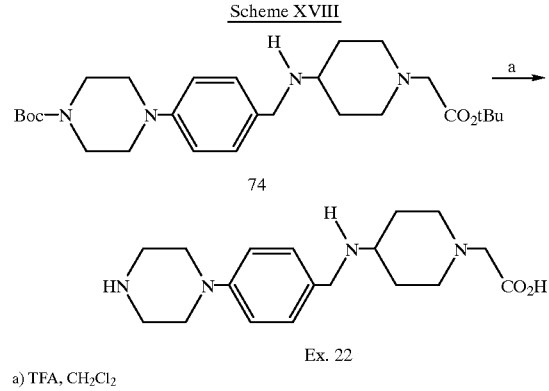

a) TFA, CH$_2$Cl$_2$

Scheme XVIII provides a method for preparing 4-piperazinylaryl-4-methylamino-piperidineacetic acids described by Formula (1), where Het$^1$ is piperazine and Het$^2$ is is an aryl group, X is an N-methylamino group, A$^1$ is CH and A$^2$ is N, and Q is a single bond. Accordingly, the protecting groups on the preparing 4-piperazinylaryl-4-methylamino-piperidineacetic acids, such as compound 74, described by Scheme 16 are removed by methods known in the art to give the desired methyl amino compounds, as exemplified by the title compound of Example 22.

Scheme XIX

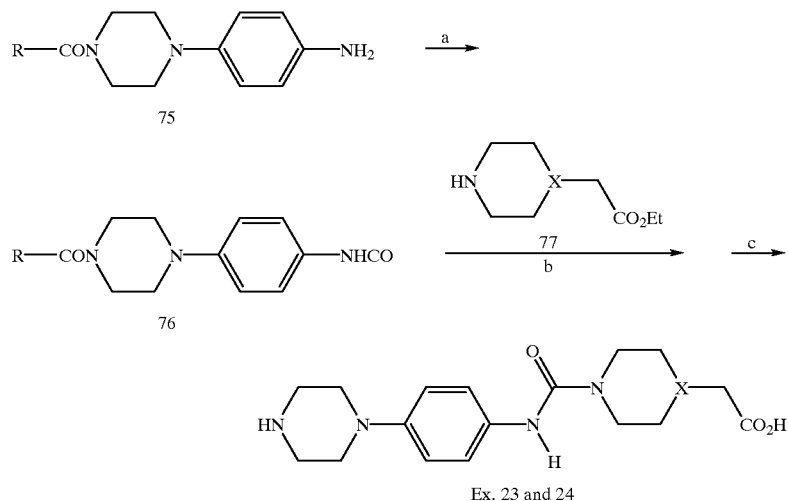

Ex. 23:
R = CF$_3$—, X = N
a) Cl$_3$COCOCl, Et$_3$N, dioxane;
b) THF;
c) 1N NaOH, MeOH Ex. 24:
R = tBuO, X = CH
a) diphosgene, Et$_3$N, dioxane;
b) Et$_3$N, THF;
c) 1. TFA, CH$_2$Cl$_2$, 2. 1 N NaOH, EtOH;
d) H$_2$ 50 psi/PtO$_2$, HCl, MeOH

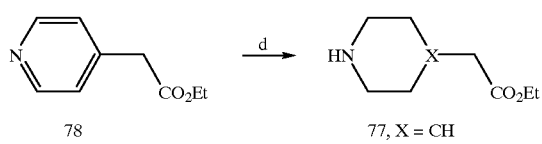

Scheme XIX provides a method for preparing ureas described by Formula (1), where Het¹ is piperazine and Het² is is an aryl group, X is an amide group, A¹ is N and A² is N or CH, and Q is a single bond. Accordingly, an isocyanate, such as compound 76, prepared from an acyl-piperazinylaniline, such as compound 75, is treated with a piperazineacetic acid ester (prepared in Scheme II) to give the protected urea. Protecting group removal affords the desired compound as exemplified in the title compounds of Example 23 and 24. When X=CH, the intermediate, such as compound 77, may be obtained from reduction of a pyridineacetic acid ester, such as 78.

Scheme XX provides a method for preparing 1-hydroxy-4-[4-(piperazinylaryl)amido]-cyclohexane-1-acetic acids described by Formula (1), where Het¹ is piperazine and Het² is is an aryl group, X is an amide group, A¹ is CH and A² is CHOH, and Q is a single bond. Accordingly, a 4-acylpiperazinylaniline (prepared in Scheme I) is treated with an active acyl derivative of 4-oxo-cyclohexanoic acid, prepared from the commercially available ester, to give an amide, such as compound 81. Addition of the lithium enolate of an alkylacetate prepared with LiN(TMS)$_2$ to the ketone, exemplified by compound 81, gives the tertiary alcohol, exemplified by compound 82. Protecting group removal affords both diastereomers of the 1-hydroxy-4-acylcyclohexaneacetic acid, as exemplified by the title compound of Examples 25 and 26.

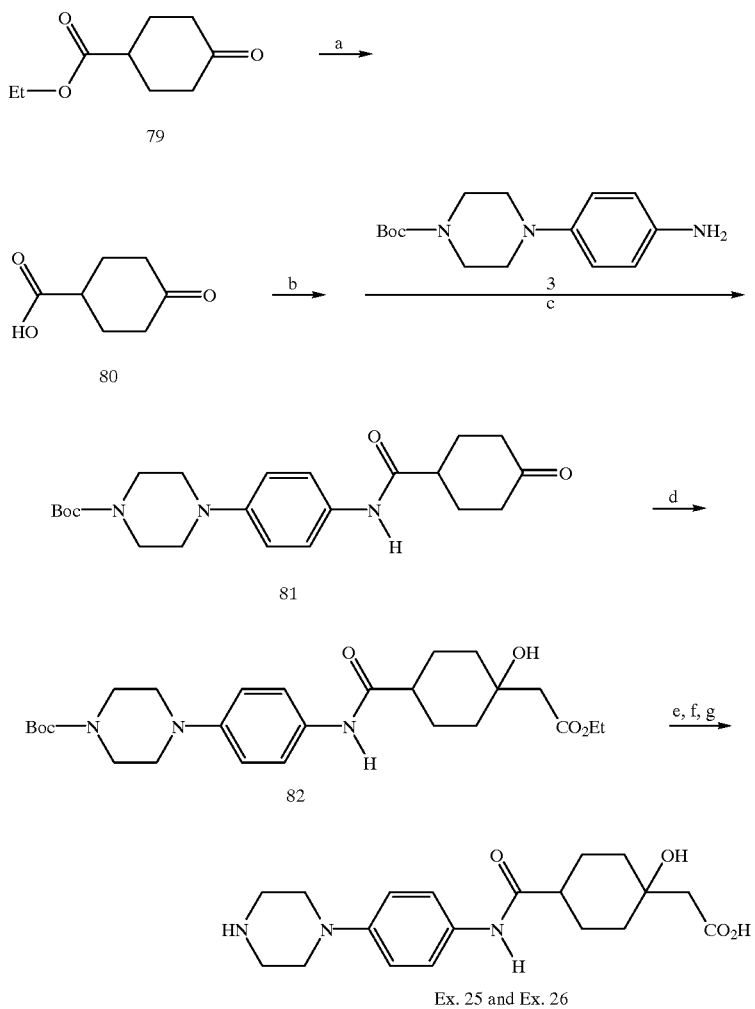

Ex. 25 and Ex. 26 a) 2% H$_2$SO$_4$;
b) SOCl$_2$, CH$_2$Cl$_2$, DMF;
c) Et$_3$N, CH$_2$Cl$_2$;
d) EtOAc/Li, N(TMS)$_2$, THF;
e) TFA, CH$_2$Cl$_2$;
f) 1N NaOH;
g) Semi-preparative hplc

Scheme XXI

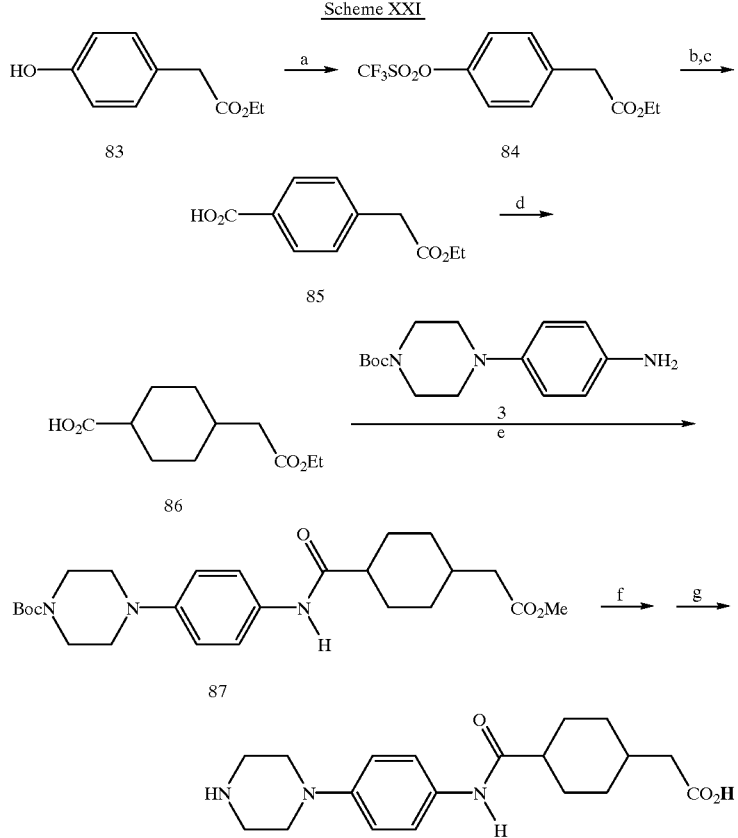

a) $CF_3SO_2O$, Pyridine/$CH_2Cl_2$;
b) 1. CO/Pd(Ac)$_2$/KOAc/1,1'-bis(Ph$_2$P)ferrocene, DMSO, 60°;
c) 0.5 N HCl;
d) H$_2$ 50 psi/PtO$_2$, HOAc;
e) EDC/HOBt, DIEA, DMF;
f) 4 M HCl/Dioxane;
g) 1N NaOH, EtOH Scheme XXI also provides a method for preparing 4-[4-(piperazinylaryl)amido]-cyclohexane-1-acetic acids described by Formula (1), where Het$^1$ is piperazine and Het$^2$ is is an aryl group, X is an amide group, A$^1$ is CH and A$^2$ is CH, and Q is a single bond. Accordingly, the 4-triflate prepared from a 4-hydroxyphenylacetic acid ester is treated with a mixture of palladium(bis)acetate, potassium acetate and 1,1'-bis(diphenylphosphine)ferrocene in an atmosphere of carbon monoxide. Acid quench of the mixture affords the 4-carboxyphenylacetic acid ester, as exemplified by compound 85. Catalytic reduction affords the 4-carboxy-cyclohexaneacetic acid ester, which is condensed with a 4-acylpiperazinylaniline (prepared in Scheme I) by methods known to the art to provide the protected amide, such as compound 87. Protecting group removal affords the desired compound as exemplified in the title compound of Example 27.

Scheme XXII

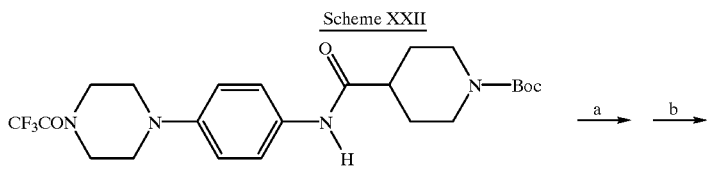

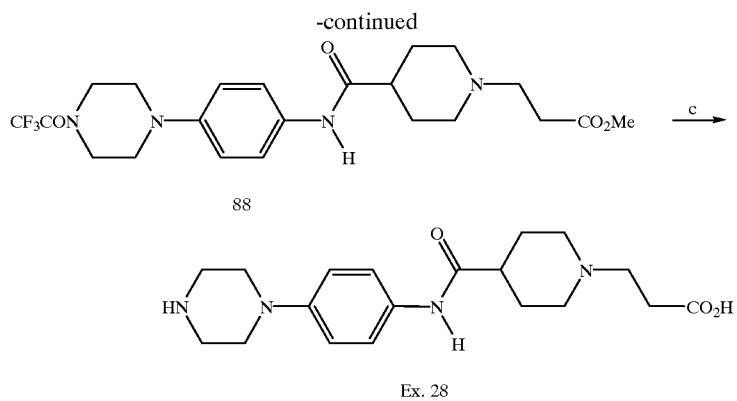

a) 4 M HCl/Dioxane;
b) Br—CH$_2$CH$_2$CO$_2$Me, Et$_3$N/DMF;
c) 1N NaOH, MeOH

Scheme XXII provides a method for preparing 4-[4-(piperazinylaryl)amido]-piperidine-alkanoic acids described by Formula (1), where Het$^1$ is piperazine and Het$^2$ is is an aryl group, X is an amide group, A$^1$ is CH and A$^2$ is N, and Q is a single bond. Accordingly, the acyl protecting group in the acylpiperidine exemplified by compound 20 (prepared in Scheme VII) is removed by methods known in the art, and alkylated with a haloalkanoic acid ester to provide the piperidinealkanoic acid ester exemplified by compound 88. Protecting group removal affords the desired compound, as exemplified by the title compound in Example 28.

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form amide bonds are generally well known to the art. The methods of peptide synthesis generally set forth by Bodansky et al., *THE PRACTICE OF PEPTIDE SYNTHESIS*, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formation of amide or peptide bonds is accomplished using conventional methods used to form amide bonds. Typically, the amine or aniline is coupled via its free amino group to an appropriate carboxylic acis substrate using a suitable carbodiimide coupling agent, such as N,N'dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

The reactive functional groups of the sidechains of each synthetic fragment are suitably protected as known in the art. Suitable protective groups are disclosed in Greene, *PROTECTIVE GROUPS IN ORGANIC CHEMISTRY*, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (e.g., 4-methoxy-benzyl or 2,4-dimethoxy-benzyl) is used to protect the mercapto group or the hydroxyl group. A suitably substituted carbobenzyloxy group or benzyl group may be also used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or HF treatment, as known in the art.

Acid addition salts of the compounds of this invention are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and NH$_4$+ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, the compounds of this invention may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds of this invention may be used in vitro to inhibit the aggregation of platelets in blood and blood products, e.g., for storage, or for ex vivo manipulations such as in diagnostic or research use.

This invention also provides a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyperaggregability, such as disseminated intravascular coagulation (DIC), septicemia, surgical or infectious shock, postoperative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor.

The compounds of formula (I) are administered either orally or parenterally to the patient, in a manner such that the concentration of drug in the plasma is sufficient to inhibit platelet aggregation, or other such indication. The pharmaceutical composition containing the compound is administered at a dose between about 0.2 to about 50 mg/kg in a manner consistent with the condition of the patient. For acute therapy, parenteral administration is preferred. For persistent states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound of this invention is administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a compound of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of formula (I) is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the compound of this invention may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor; their ability to inhibit platelet aggregation, in vitro, and their ability to inhibit thrombus formation in vivo.

Inhibition of RGD-mediated GPIIb-IIIa binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70° C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 μg/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 μg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μg unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]-SK&F-107260 used in the competitive binding assay (4.5 nM), and Kd is the dissociation constant of [3H]-SK&F-107260 which is 4.5 nM as determined by Scatchard analysis. 4-[[[4-(1-Piperazinyl)phenyl]amino]-carbonyl]-1-piperidineacetic acid, which is a compound of this invention, inhibits [3H]-SK&F 107260 binding with a Ki of about 0.005 μM.

Inhibition of Platelet Aggregation

Inhibition of platelet aggregation was determined following the procedure described in Nichols, et al., *Thrombosis Research*, 75, 143 (1994). Blood was drawn from the antecubital vein of normal human volunteers who had not taken a cyclooxygenase inhibitor within the previous 14 days into a plastic syringe containing one part 3.8% trisodium citrate to nine parts blood. Platelet rich plasma was prepared by centrifuging the blood at 200 g for 10 min at RT. The platelet rich plasma was drawn off and the remaining blood was centrifuged at 2400 g for 5 min at RT to make platelet poor plasma. Platelet count was measured with a model ZB1 Coulter Counter (Coulter Electronics Inc., Hialeah, Fla.) and was adjusted to 300,000/μl using platelet poor plasma. Platelet aggregation was studied in a Chrono-Log model 400VS Lumi Aggregometer (Chrono-Log, Havertown, Pa.) using platelet rich plasma stirred at 1200 r.p.m. and maintained at 37° C., with platelet poor plasma as the 100% transmission standard. Concentration-response curves for the ability of compounds to inhibit platelet aggregation, measured as the maximum change in light transmission, induced by a maximal concentration of adenosine diphosphate (10 μM) were constructed and the $IC_{50}$ was determined as the concentration of antagonist required to produce 50% inhibition of the response to the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

The examples which follow are intended to in no way limit the scope of this invention, but are provided to illustrate how to make and use the compounds of this invention. Many other embodiments will be readily apparent and available to those skilled in the art.

EXAMPLE 1

Preparation of 4-[[[4-(1-piperazinyl)phenyl]amino] carbonyl]-1-piperidineacetic acid a) methyl 4-piperidinecarboxylate hydrochloride Isonipecotic acid (40 g, 310 mmol) was suspended, with stirring, in 250 mL of dry methanol and treated with HCl gas (lecture bottle) until solution was obtained. The solution was then cooled in an ice bath and treatment with HCl gas continued for an additional 20 min. After 2.5 h, the reacion mixture was stripped of solvent using a water aspirator (30° C.) and the resulting heavy, white cake suspended in 150 mL dry THF and filtered. The filter cake was washed with two portions of 50 mL THF, followed by washing with 3×50 ml $Et_2O$, dried briefly in air (suction). The pale-yellow filtrate was discarded. Drying the slightly off-white solid was completed over-night in a desiccator ($CaSO_4$) under high vacuum. The title compound (43.25 g) was obtaind analytically pure. Anal. ($C_7H_{14}ClNO_2$) calcd: C, 46.80; H, 7.86; N, 7.80; Cl, 19.73. found C, 46.66; H, 7.78; N, 19.82. TLC Rf=0.63 (silica gel, 3:1 ethanol/conc. aq. ammonium hydroxide).

b) 1,1-dimethylethyl-4-(methoxycarbonyl)-1-piperidineacetate

The compound of example 1(a) (1.8 g, 10 mmol) was vigorously stirred with $K_2CO_3$ (1.4 g, 10 mmol) and N,N'-diisopropylethylamine (1.74 mL, 10 mmol) in 60 mL of acetone under a slight positive pressure of argon. To this mixture was added t-butyl chloroacetate (1.6 g, 10 mmol) in 10 mL acetone during ~15 min and then the reaction mixture was gently refluxed for 5 h. After cooling in ice, the mixture was filtered and the solids washed with acetone. The pale yellow filtrate was stripped of solvent and the residue taken up in a mixture of diethylether (100 mL) and water (10 mL). The organic layer was washed successively with water, sat. $Na_2CO_3$, water, and brine, dried ($MgSO_4$) and stripped of solvent. Removal of solvent and other volatiles was continued overnight in a constant high vacuum, at 50° C., to yield the title compound as a light yellow liquid (1.2 g) that was analytically pure. Anal. $C_{13}H_{23}NO_4$) calcd: C, 60.68; H, 9.01; N, 5.44. found: C, 60.28; H, 8.91; N, 5.60. MS (ES), $(M+H)^+=258.0$.

c) sodium N-[(t-butyloxycarbonyl)methyl]piperidine-4-carboxylate

The compound of example 1(b) (0.78 g, 3 mmol) was dissolved in 3 mL of methanol and treated with ca. 3 mL 1N NaOH overnight. A small fraction of ester remaining (TLC) was saponified by adding 0.3 mL 1 N NaOH and heating in a water bath (50° C.) for 2 h, leaving only a trace of the ester (TLC). The reaction mixture was evaporated to dryness on a flash-evaporator, followed by azeotropic drying with toluene and high vacuum at 50° C. overnight. The title compound (0.72 g; crude) was used without purification. MS (ES), $(M+H)^+=244.0$. TLC Rf 0.64 (silica gel, 1:1:1:1 ethyl acetate, n-butanol, acetic acid, water).

d) 1-t-butoxycarbonyl-4,4'-nitrophenylpiperazine 1-(4-Nitrophenyl)piperazine (Spectrum Chemical Corp.; 20.7 g, 100 mmol) was suspended in 200 mL of methylene chloride and the dark mixture was stirred in an ice bath under argon. To this cold suspension was added, in portions, solid di-t-butyl dicarbonate (26.2 g, 120 mmol). After stirring in ice for a half hour, when vigorous gas evolution subsided and most of the solid had entered solution, the ice bath was removed and stirring continued at rt for an additional 3.5 h. The dark solution was filtered, washed with 4 portions of water (50 mL) and brine (50 mL), filtered through a pad of $MgSO_4$ and the solvent evaporated in vacuo. The title compound is obtained as an orange-yellow solid (27.7 g) showing only trace impurities by TLC. MS (ES), $(M+H)^+=308.0$ Crystallization (26 g) from methanol/water yields analytically pure compound (20 g). mp 144.5–145.5° C. Anal. ($C_{15}H_{21}N_3O_4$) calcd: C, 58.62; H, 6.89; N, 13.67. found: C, 58.76; H, 6.79; N, 13.59.

e) 1-t-butoxycarbonyl-4,4'-aminophenylpiperazine hydrochloride

The compound of example 1(d) (0.91 g, 3 mmol) was dissolved in 100 mL 95% ethanol in a Paar vessel, the yellow solution cooled in an ice bath and mixed with 3 mL 1N HCl and 5% palladium on carbon (90 mg). The mixture was hydrogenated on a Paar Shaker ($H_2$, 48psi, rt) until after a theoretical amount of hydrogen was consumed in the reaction. The colorless solution was taken to dryness (aspirator) to obtain a an off-white solid, which was kept in a high vacuum overnight. The title compound (0.93 g) darkens on exposure to light and air. MS (ES) $(M=H)^+=278.2$; TLC Rf 0.26 (silica gel, 3% methanol/chloroform).

f) 4-[[[4-(1-piperazinyl)phenyl]amino]carbonyl]-1-piperidineacetic acid trifluoroacetate To a stirred, ice-cold suspension of the compound of example 1(e) (0.5 g, 1.5 mmol) and the compound of example 1(c) (0.44 g, 1.7 mmol) in 8 mL DMF and 0.42 mL triethylamine (3 mmol) was added solid 2-(1H-benzotriazol-1-yl)-1,1,3,3-tetramethyluronium hexafluorophosphate and the mixture left stirring in an ice-bath. After 1 h the ice bath was removed, triethylamine (0.42 mL, 3 mmol) was added to bring the mixture to ~pH 9 and stirring continued overnight at rt, under argon, and for an additional day at 50° C. The reaction mixture was stripped of solvent in vacuo and the residue extracted with diethylether, filtered, the ether extract washed with water, sat. $NaHCO_3$, and brine, dried over $Na_2SO_4$ and the solvent evaporated in vacuo. The remaining lt. orange solid (0.5 g) was taken up in 20 mL of methylene chloride and treated with 20 mL TFA, and stirred under argon for 2 h. After the volatiles were removed in vacuo, this treatment was repeated and the solid remaining after the solvent was evaporated was dissolved in 10 mL water and purified, portion-wise, by RPHPLC (Vydac $C_{18}$ support; 0.1% TFA-5% acetonitrile in water). The major component was collected and lyophilized to obtain the title compound as a (hygroscopic) white powder. TLC Rf 0.18 (silica gel; ethyl acetate: n-butanol: acetic acid: water,1:1:1:1). RPHPLC k' 5.8 (Vydac C18, gradient A: 0.1% TFA-water B 0.08% TFA-acetonitrile, 5–50% acetonitrile during 20 min). MS (ES) $(M+H)^+=347$. $H^1$ NMR (400 MHz, methanol-$d^4$) 7.48 (d, 2H, J=9 Hz ), 7.00 (d, 2H, J=9Hz), 4.09 (s, 2H), 3.73 (br s, 2H), 3.35 (s, 8H), 3.15 (br s, 2H), 2.71 (brs, 1H), 2.13 (brs,4H).

EXAMPLE 2

Preparation of Methyl 4-[[[4-(1-piperazinyl)phenyl]amino]carbonyl]-1-piperidine acetate a) Methyl 4-[[[4-(4-t-butyloxycarbonyl-1-piperazinyl)phenyl]amino]carbonyl]-1-piperidine acetate A mixture of Methyl-4-carboxy-1-acetate (3.0 g, 12.6 mmol), $Et_3N$ (5.7 mL, 55 mmol), 4-(4-aminophenyl)-1-t-butyloxycarbonylpiperazine (3.0 g, 8.6 mmol) in $CH_3CN$ (50 mL) was treated with HATU (5.0 g, 13.1 mmol). Solution was stirred at RT for 10 hr. Solution was concentrated and residue was precipitated from $MeOH/AcOH/H_2O$ (20 mL/0.1 mL/60 mL) to give the title compound (3.4 g, 75%). MS (ES) m/e 461 $[M+H]^+$.

b) Methyl 4-[[[4-(1-piperazinyl)phenyl]amino]carbonyl]-1-piperidine acetate

A solution of Methyl 4-[[[4-(4-t-butyloxycarbonyl-1-piperazinyl)phenyl]amino]carbonyl]-1-piperidine acetate (2.1 g, 4.5 mmol) was treated with $CH_2Cl_2/TFA$ (10 mL/15 mL) for 20 min. Solution was concentrated and the residue was treated with MeOH/4M HCl (10 mL/10 mL). Solution was concentrated until precipitation started. Solution was filtered and the solid was washed with $Et_2O$ to give the title compound (1.5 g, 87%). MS (ES) m/e 361 $[M+H]^+$. $^1$HNMR (250 MHz, DMSO[d6]) δ 1.4–4.5 (m, 22H), 6.9–9.5 (m, 5H). Anal. $(C_{18}H_{25}N_3O_3 \cdot 2.87HCl \cdot 0.5H_2O)$ calcd: C, 54.32; H, 7.20; N, 10.29. found: C, 54.52; H, 7.24; N, 10.35.

EXAMPLE 3

Preparation of Ethyl-4-[[[4-(1-Piperazinyl)phenyl]amino]carbonyl]-1-piperidine acetate a) Ethyl-4-[[[[4-(1-(tert-butoxycarbonyl)piperazinyl]phenyl]amino]carbonyl]-1-piperidine acetate 16

EDC (1.69 g, 8.8 mmole) was added to a solution containing of 4-[1-(tert-butoxycarbonyl)piperazinyl]aniline 3 (2.22 g, 8 mmol), $HOBT \cdot H_2O$ (1.19 g, 8.8 mmole), ethyl 4-carboxypiperidinyl acetate 8 (1.72 g, 8 mmol) and diisopropylethylamine (1.82 mL, 10.4 mmole) in anhydrous DMF (20 mL) at RT. After 20 hr the reaction was concentrated on the rotavap (high vacuum). The residue was dissolved in $CH_2Cl_2$, and silica gel chromatography (2% $MeOH/CH_2Cl_2$) gave the title compound (2.73 g, 72%): MS (ES) m/e 475.2 $(M+H)^+$.

b) Ethyl-4-[[[4-(1-Piperazinyl)phenyl]amino]carbonyl]-1-piperidine acetate

The compound of 3(a) (2.6 g, 5.48 mmol) was dissolved in $CH_2Cl_2$ (30 mL) and treated with HCl (4M in dioxane, 60 mL) for 2 h. The solvent was removed on rotavap and left an off white solid: MS (ES) m/e 375.2 $(M+H)^+$. Anal. Calcd for $C_{20}H_{30}N_4O_3 \cdot 3.1$ HCl C, 49.27; H, 6.84; N, 11.49; Cl, 22.54. Found: C, 49.16; H, 6.93; N, 11.2; Cl, 22.69.

EXAMPLE 4

Preparation of 4-[[[4-(1-N-ethyloxycarbonyl-4-piperazinyl)phenyl]amino]carbonyl]-1-piperidine-methyl acetate a) 4-[(1-N-ethyloxycarbonyl)piperazinyl]-nitrophenol Ethylchloroformate (2.5 mL, 24.3 mmol) was added to a cooled solution of 4-piperazinyl nitrophenol (5.0 g, 24.1 mmol) and $Et_3N$ (6.7 mL, 24.1 mmol) in $CH_2Cl_2$ (100 mL). Reaction was stirred at RT for 18 h. Reaction was washed with 5% $NaHCO_3$ and $H_2O$. Organic layer was concentrated to give the title compound (6.27 g, 94%) MS (ES) m/e 280 $[M+H]^+$.

b) 4-[(1-N-ethyloxycarbonyl)piperazinyl]-aniline

A mixture of compound of Example 4(a) (3.0 g, 10.8 mmol) and 10% Pd/C (1.0 g) in EtOH/DMF (20 mL/30 mL) was hydrogenated at 45 psi for 1 h. Reaction was filtered through Celite and the filtrate was concentrated to afford title compound (2.85 g, 100%). MS (ES) m/e 250 $[M+H]^+$.

c) 4-[[[4-[4-(ethyloxycarbonyl)-1-piperazinyl]phenyl]amino]carbonyl]-1-t-butyloxycarbonyl-piperidine A solution of 4-(ethyloxycarbonyl)-1-piperazinylphenylamine (2.7 g, 10.8 mmol), 1-t-butyloxycarbonyl-4-carboxypiperidine (2.5 g, 10.8 mrnol), HOBt (1.6 g, 10.8 mmol) and $Et_3N$ (2.0 mL, 15 mmol) was treated with EDC (2.1 g, 10.8 mmol). Solution was stirred at RT for 18 hr. Solution was concentrated and the residue was partitioned between EtOAc and $H_2O$. EtOAc layer was separated and washed successively with 5% citric acid (2×), $H_2O$ (1×), 5% $NaHCO_3$ (2×), $H_2O$ (1×), brine (1×). EtOAc was dried over $Na_2SO_4$, filtered and concentrated to give the title compound (4.69 g, 94%). MS (ES) m/e 461 $[M+H]^+$.

d) 4-[[[4-[4-(ethyloxycarbonyl)-1-piperazinyl]phenyl]amino]carbonyl]piperidine

A solution of compound of Example 4(c) (1.0 g, 2.2 mmol) in HCl/Dioxane (4M, 15 mL) was stirred at RT for 1 h. Reaction was concentrated and the residue was treated with $Et_2O$. Solution was filtered and the solid was dried in vacuo to afford the title compound (0.86 g, 100%). MS (ES) 361 $[M+H]^+$.

e) Methyl-4-[[[4-[4-(ethyloxycarbonyl)-1-piperaziny]phenyl]amino]carbonyl]-1-piperidine acetate To a solution of 4-[[[4-[4-(ethyloxycarbonyl)-1-piperazinyl]phenyl]amino]carbonyl]piperidine (0.87 g, 2.2 mmol) and $Et_3N$ (0.6 mL, 4.4 mmol) in DMF (10 mL) was added methyl bromoacetate (0.208 mL, 2.2 mmol). After 18 h solution was concentrated. Residue was taken up in EtOAc and washed with 5% $NaHCO_3$. EtOAc layer was separated and concentrated to give, the title compound (0.40 g, 50%). $^1$HNMR (250 MHz, DMSO[d6]) δ 1.0–4.2 (m, 26H), 6.8–7.5 (d, 4H), 9.6 (s, 1H). MS (ES) m/e 433 $[M+H]^+$. Anal. $(C_{22}H_{32}N_4O_5)$ calcd: C, 61.09; H, 7.46; N, 12.95. found: C, 61.15; H, 7.53; N, 12.92.

EXAMPLE 5

Preparation of 4-[[[4-(1-N-ethyloxycarbonyl-4-piperazinyl)phenyl]amino]carbonyl]-1-piperidine acetic acid a) 4-[[[4-(1-N-ethyloxycarbonyl-4-piperazinyl)phenyl]amino]carbonyl]-1-piperidine acetic acid To a solution of Methyl-4-[[[4-[4-(ethyloxycarbonyl)-1-piperaziny]phenyl]amino]carbonyl]-1-piperidine acetate (0.84 g, 1.9 mmol) and $MeOH-H_2O$ (1/1, 10 mL) was added 1N NaOH (2.2 mL, 2.2 mmol). After 18 hr solution was concentrated. $H_2O$ was added followed by AcOH to pH 4 (litmus paper). Solution was placed in the refrigerator. Filtration gave the title compound (0.27 g, 33%). $^1$HNMR (250 MHz, DMSO[d6] δ 1.2–4.2 (m, 24H), 6.8–7.6 (dd, 4H), 9.7 (s, 1H). MS (ES) m/e 419 $[M+H]^+$. Anal. $(C_{21}H_{30}N_4 \cdot 2H_2O)$ cald: C, 55.49; H, 7.54; N, 12.33. found: C, 55.63; H, 7.51; N, 12.29.

EXAMPLE 6

Preparation of 4-[[[4-(4-Methyl-1-piperazinyl)phenyl]amino]carbonyl]-1-piperidine acetic acid a) t-Butyl-4-[[[4-(4-N-trifluoroacetyl-1-piperazinyl)phenyl]amino]carbonyl]-1-piperidine acetate A solution of 4-(4-N-trifluoroacetyl-1-piperazinyl)phenyl]amine (0.8 g, 3 mmol), t-butyl-4-carboxy-1-piperidine acetate (0.8 g, 3 mmol), $Et_3N$ (1.3 mL, 9.0 mmol) in $CH_3CN$ (25 mL) was treated with HATU (1.25 g, 2.2 mmol). Solution was stirred at RT for 18 hr. Solution was concentrated. Residue was taken up in EtOAc and washed successively with 5% NaHCO$_3$, H$_2$O. Solution was concentrated and the residue was treated with hot EtOAc. Cooling to RT gave precipitation which was filtered to give the title compound (0.86 g, 50%). MS (ES) m/e 499 [M+H]$^+$.

b) t-Butyl-4-[[[4-(1-piperazinyl)phenyl]amino]carbonyl]-1-piperidine acetate

A solution of t-Butyl-4-[[[4-(4-N-trifluoroacetyl-1-piperazinyl)phenyl]amnino]carbonyl]-1-piperidine acetate (0.89 g, 1.5 mmol), in EtOH (5 mL) was treated with 1N NaOH (1.5 mL, 1.5 mmol). After 18 hr solution was concentrated to give the title compound (0.53 g, 40%). MS (ES) m/e 289 [M+H]$^+$.

c) t-Butyl-4-[[[4-(4-methyl-1-piperazinyl)phenyl]amino]carbonyl]-1-piperidine acetate A stirred mixture of compound of Example 6(b) (0.89 g, 1.49 mmol), Pd/C (5%, 0.1 g) and Formaldehyde (77% soln., 0.15 mL, 1.9 mmol) was hydrogenated at 35 psi for 4 h. Reaction was filtered and the filtrate was concentrated to afford the title compound (0.95 g, 80%). MS (ES) m/e 305 [M+H]$^+$ d) 4-[[[4-(4-methyl-1-piperazinyl)phenyl]amino]carbonyl]-1-piperidine acetic acid A solution of t-Butyl-4-[[[4-(4-methyl-1-piperazinyl)phenyl]amino]carbonyl]-1-piperidine acetate (0.53 g, 1.3 mmol) in 1,4-dioxane (2 mL) was treated with 4M HCl (20 mL). After 3.5 hr solution was concentrated. Residue was purified by prep. HPLC (C-18 reversed phase, 5% CH$_3$CN, 0.1% TFA, H$_2$O ) to givethe title compound (0.21 g, 50%). MS (ES) m/e 361 [M+H]$^+$. $^1$HNMR (250 MHz, DMSO[d6]) δ 1.5–4.5 (m,21H), 6.9–9.5 (m, 5H). Anal. (C$_{19}$H28N$_4$O$_3$.3.25TFA) calcd: C, 42.00; H, 4.01; N, 7.56. found: C, 42.14; H, 4.21; N, 7.86.

EXAMPLE 7

Preparation of Sodium 4-[[[4-[4-(phenylmethyl)-1-piperazinyl]phenyl]-carbonyl]aminol-1-piperidine acetate a) 1-benzyl-4-(4-cyanophenol)piperazine A solution of 4-fluorobenzonitrile (3.6 g, 29.7 mmol) and 1-benzylpiperazine (7.5 g, 42.6 mmol) was refluxed for 24 h. Toluene was added and washed consecutively with water, brine, dried over Na$_2$SO$_4$. Solution was concentrated to give the title compound (0.76 g, 10%). MS (ES) m/e 278 [M+H]$^+$ b) 1-benzyl-4-(4-carboxyphenol)piperazine A solution of compound of Example 7(a) (5 g, 18 mmol) in NaOH solution (51% (w/v) in water) was refluxed for 24 h. Reaction was cooled and treated with HCl (6 N, 80 mL). Reaction was filtered and solid was dried to give title compound (1.9 g, 40%). MS (ES) m/e 297 [M+H]$^+$.

c) 1-benzyl-4-(4-chlorocarbonylphenol)piperazine

A solution of 1-benzyl-4-(4-carboxyphenol)piperazine (1.34 g, 3.47 mmol) in CH$_2$Cl$_2$ (20 mL) was treated with thionyl chloride (1 mL, 35 mmol). Solution was refluxed for 1 hr. Solution was concentrated to an oil which was used as is for the next step (1.9 g, Quant.)

d)Methyl 4-[[[4-[4-(phenylmethyl)-1-piperazinyl]phenyl]carbonyl]amino]-1-piperidine acetate A cold solution of 1-benzyl-4-(4-chlorocarbonylphenol)piperazine (1.9 g, 3.5 mmol) and Et$_3$N (0.5 mL, 3.5 mmol) in CH$_2$Cl$_2$ (40 mL) was added at once to a cold solution of methyl-4-aminopiperidine acetate (0.7 g, 1.5 mmol) in CH$_2$Cl$_2$ (20 mL). After 4 hr of stirring at RT solution was filtered. Filtrate was washed successively with 5% Na$_2$CO$_3$ (2×), H$_2$O (2×) and dried over Na$_2$SO$_4$. Filtration and concentration gave a residue which was purified by flash silica gel chromatography (CHCl$_3$/MeOH/Et$_3$N 95:4:1) to give the title compound (0.47 g , 25%). MS (ES) m/e 451 [M+H]$^+$.

e) Sodium4-[[[4-[4-(phenylmethyl)-1-piperazinyl]phenyl]carbonyl]amino]-1-piperidine acetate To a solution of compound of Example 7(d) (0.47 g, 1.04 mmol) in MeOH (5 mL), acetone (5 mL) was added 1N NaOH (1.12 mL, 1.12 mmol). Reaction was heated to 50° C. for 40 min. Reaction was cooled and filtered to give the title compound (0.3 g, 80%). MS (ES) m/e 437 [M+H]$^+$. $^1$HNMR (250 MHz, DMSO[d6]) δ 1.5–4.5 (m, 21H), 6.8–9.5 (m, 10H). Anal. (C$_{25}$H$_{31}$N$_4$O$_3$.0.5H$_2$O ) calcd: C, 63.78; H, 6.80; N, 11.71. found: C, 63.98; H, 6.77; N, 11.92.

EXAMPLE 8

Preparation of 4-[[[4-(4-piperidinyl)phenyl]amino]carbonyl]-1-piperidineacetic acid a) 4-(4-pyridinyl)nitrobenzene 33

The title compound was prepared in 34% yield according to R. Forsyth and F. L. Pyman, J. Chem. Soc. Perkin Trans II, 1926, 2912–24. MS (ESI) m/e 201.0 [M+H]$^+$. $^1$H NMR (400 MHz, DMSO-D6) δ 9.05(d, 2H), 8.5 (d, 2H), 8.45 (d, 2H), 8.3 (d, 2H). HPLC k' 5.58 (Ultrasphere® ODS, gradient , A:acetonitrile B:water-0.1% trifluoroacetic acid, 5–60% acetonitrile during 20 min; UV detection at 220 nm). Anal. (C$_{11}$H$_8$N$_2$O$_2$.3H$_2$O ) calcd: C, 45.49; H, 5.2; N, 9.64. Found: C, 45.56; H, 4.99; N, 9.47.

b) 4-(4-pyridinyl)aniline hydrochloride 34

To a solution of Example 8(a) (2.4 g, 10 mmol) in DMF (70 mL) was added 10% Pd/C (0.75 g) under argon. The solution was hydrogenated under 50 psi for 1 h. The solution was filtered through celite, and concentrated to afford the title compound as yellow solid (1.63 g, 79%). MS (ESI) m/e 171.0 [M+H]$^+$. TLC R$_f$ 0.63 (silica gel, 1:1 hexane:ethyl acetate). HPLC k' 1.88 (Ultrasphere® (ODS, gradient , A:acetonitrile B:water-0.1% trifluoroacetic acid, 5–60% acetonitrile during 20 min; UV detection at 220 nm).

c) Ethyl-4-[[[4-(4-pyridinyl)phenyl]amino]carbonyl])-1-piperidine acetate 35

EDC (636 mg, 3.3 mmol) was added to a solution of the compound of Example 8(b) (682 mg, 3.3 mmol), ethyl-4-carboxypiperidine acetate 14 (646 mg, 3 mmol), HOBt. H$_2$O (446 mg, 3.3 mmol) and DIEA (1.2 mL, 6.8 mmol) in anhydrous DMF (10 mL) at RT. After stirring for 20 h, the reaction was concentrated on rotavap (high vacuum). The resulting residue was taken into EtOAc and washed successively with H$_2$O (3×20 mL), 10% NaHCO3 (2×20 ml) and saturated NaCl. The organic extract was dried (anhydrous Na$_2$SO$_4$), filtered and concentrated to yield the title compound (350 m g, 32%) as a yellow solid. HPLC k' 5.3 (Ultrasphere® ODS, gradient , A:acetonitrile B:water-0. 1% trifluoroacetic acid, 5–60% acetonitrile during 20 min; UV detection at 220 nm). MS (ESI) m/e 368.2[M+H]$^+$.

d) Ethyl-4-[[[4-(4-piperidinyl)phenyl]amino]carbonyl])-1-piperidine acetate 36

To a solution of the compound of Example 8(c) (260 mg, 0.7 mmol), in methanol (15 ml ) was added PtO$_2$ (150 mg, 0.66 mmol) and HCl (2 mL of 1N) under argon. The solution was hydrogenated under 47 psi for 4 h. The solution was filtered through celite, concentrated and triturated with ethyl acetate to afford the title compound as off white solid (30 mg). MS (ESI) m/e 374.2 [M+H]$^+$. $^1$H NMR (400 MHz, DMSO-D6) δ 10.25 (brs, 1H), 8.8 (brs, 1H), 7.55 (d, 1H), 7.15 (d, 1H), 4.25 (q, 2H), 3.55 (brs, 2H), 3.3 (brs, 8H), 2.6–3 (m, 4H), 2.0 (m, 4H), 1.9 (m, 4H) 1.25 (t, 3H). HPLC k' 5.0 (Ultrasphere® ODS, gradient , A:acetonitrile B:water-0.1% trifluoroacetic acid, 5–60% acetonitrile during 20 min; UV detection at 220 nm). Anal. (C$_{21}$H$_{31}$N$_3$O$_3$.2 HCl.0.5H$_2$O) calcd: C, 55.38; H, 7.53; N, 9.23. Found: C, 55.16; H, 7.49; N, 9.16.

e) 4-[[[4-(4-piperidinyl)phenyl]amino]carbonyl]-1-piperidine acetic acid sodium salt To a solution of the compound of Example 8(d) (370 mg, 0.83 mmol) in 1:1 ethanol-THF mixture (20 mL) was added a solution of 1N NaOH (2.5 ml, 2.5 mmol) and was stirred at RT for 20 h. The resulting white precipitate was collected by filtration to yield the title compound (170 mg) as white solid. HPLC k' 2.38 (Ultrasphere® ODS, gradient , A:acetonitrile B:water-0.1% trifluoroacetic acid, 5–60% acetonitrile during 20 min; UV detection at 220 nm). 1H NMR (400 MHz, DMSO-D6) δ 10.05 (s, 1H), 9.9 (brs, 1H), 8.5 (dd, 1H), 7.50 (d, 2H), 7.15 (d, 2H), 4.2 (s, 2H), 3.65 (brd, 2H), 3.3 (br d, 2H), 2.95 (m, 4H), 2.75 (m, 1H), 2.55 (m, 1H), 1.7–2.0 (m, 8H). MS (ESI) m/e 346.0 [M+H]$^+$. Anal. ($C_{19}H_{26}N_3O_4$Na. 0.25 EtOH, 2.25 $H_2O$ ) calcd: C, 55.84; H, 7.69; N, 10.02. Found: C, 55.80; H, 7.56; N, 9.68.

EXAMPLE 9

Preparation of 4-[[[4-(4-pyridinyl)phenyl]amino]carbonyl]-1-piperidine acetic acid a) t-Butoxycarbonyl-4-[[[4-(4-pyridinyl)phenyl]amino]carbonyl])-1-piperidine acetate 37

EDC (316.3 mg, 1.65 mmol) was added to a solution 4-(4-pyridinyl)aniline hydrochloride 34 (342 mg, 1.65 mmol), t-butoxycarbonyl-4-carboxypiperidine acetate 12 (365 mg, 1.5 mmol), HOBt.$H_2O$ (223 mg, 1.65 mmol) and DIEA (634 μmL, 3.64 mmol) in anhydrous DMF (10 mL) at RT. After stirring for 20 h, the reaction was concentrated on rotavap (high vacuum). The resulting residue was taken into EtOAc and washed successively with $H_2O$ (3×20 mL), 10% $NaHCO_3$ (2×20 ml) and saturated NaCl. The organic extract was dried (anhydrous $Na_2SO_4$), filtered and concentrated to yield the title compound (500 mg, 84%) as a yellow solid. HPLC k' 6.35 (Ultraphere® ODS, gradient, A:acetonitrile B:water-0.1% trifluoroacetic acid, 5–60% acetonitrile during 20 min; UV detection at 220 nm). MS (ESI) m/e 396.2[M+H]$^+$.

b) Preparation of 4-[[[4-(4-pyridinyl)phenyl]amino]carbonyl]-1-piperidine acetic The compound of Example 9(a) (0.5 g, 1.29 mmol) in $CH_2Cl_2$ (10 ml) was added trifluoroacetic acid (10 ml) at RT and stirred for 5 h. The resulting solution was then concentrated to dryness on rotavap and evaporated with $CH_2Cl_2$ twice. The resulting oily residue was dissolved in $H_2O$, and the pH was adjusted to 8.45 using dilute ammonium hydroxide . The aqueous solution was purified on flash ODS column (step gradient, 2–16% acetonitrile/water. The fractions containing the pure compound were collected, concentrated and lyophilized to yield the title compound (150 mg, 35% ) as a white powder. HPLC k' 4.23 (Ultrasphere® ODS, gradient, A:acetonitrile B:water-0.1% trifluoroacetic acid, 5–60% acetonitrile during 20 min; UV detection at 220 nm). MS (ESI) m/e 340.2 [M+H]$^+$; Anal. ($C_{19}H_{21}N_3O_3$.2.25 $H_2O$ ) calcd: C, 60.07; H, 6.77; N, 11.06. Found: C, 59.76; 6.57; N, 10.88. $^1$H NMR (400 MHz, DMSO-D6.TFA) δ 10.42 (s, 1H), 9.85 (br s, 1H), 8.88 (dd, 2H), 8.38 (d, 2H), 8.05 (d, 2H), 7.82 (d, 2H), 4.15 (s, 2H), 3.6 (brd, 2H), 3.35–3.05 (brd, 3H), 2.0 (m, 4H).

EXAMPLE 10

Preparation of 4-[[5-[2-(1-Piperazinyl)pyridinyl]amino]carbonyl]-1-piperdineacetic acid a) 2-(1-tert-Butoxycarbonylpiperazinyl)-5-nitropyridine 40

A mixture of tert-butyl 1-piperazinecarboxylate (1.0 g, 5.3 mmol), 2-chloro-5-nitropyridine (0.85 g, 5.3 mmol) and triethylamine (1.58 mL, 11.0 mmol) in $CH_3$-CN (50 mL) were stirred at rm temperature for 18 hr. The yellow suspension was concentrated, the residue was taken up in $CH_2Cl_2$ (125 mL) and washed with 5% $NaHCO_3$ (2×25 mL) and brine (2×25 mL), dried over $MgSO_4$ and concentrated to dryness in vacuo to yield the yellow titled compound (1.65 g, 100%). MS (ES) m/e 309.2 [m+H]$^{+1}$.

b) 2-(1-tert-Butoxycarbonylpiperazinyl)-5-aminopyridine 41

The compound of Example 10(a) (1.65 g, 5.3 mmol) was suspended in MeOH (200 mL) in the presence of 10% Pd/C (0.17 g) and hydrogenated in a Paar shaker under a hydrogen atmosphere (40 psi) at rm temperature for 1.5 h. The catalyst was filtered and the filtrate was concentrated to yield the light-pink titled compound (1.4 g, 95%).

c) Ethyl 4-[[5-[2-[1-(tert-butoxycarbonyl)piperazinyl]pyridinyl]amino]carbonyl]-1-piperidineacetate 42

The compound of Example 10(b) (1.4 g, 5.0 mmol) and pyridine (1.1 mL) in $CH_2Cl_2$ (20 mL) was added to a suspension of the acid chloride in $CH_2Cl_2$ (10 mL) obtained from refluxing 1-ethoxycarbonylmethyl-4-piperidinecarboxylic acid hydrogen chloride (1.1 g, 4.3 mmol) in $SOCl_2$ (10 mL) for 15 min, followed by removal of $SOCl_2$. After 18 h, the reaction mixture was poured into 5% $NaHCO_3$ (75 ml) and extracted with $CH_2Cl_2$ (3×20 mL). The combined organic fractions were backwashed with 5% $NaHCO_3$ (2×50 mL) and brine (2×50 mL), dried over $MgSO_4$ and concentrated. The semi-solid was triturated with EtOAc to give the title compound (1.25 g, 60%). MS (ES) m/e 476.2 [m+H]$^+$. Anal. Calcd. for $C_{24}H_{37}N_5O_5$: C, 60.61; H, 7.84; N, 14.73; Found C, 60.58; H, 7.76; N, 14.65.

d) 4-[[5-[2-(1-Piperazinyl)pyridinyl]amino]carbonyl]-1-piperidineacetic acid

The compound of Example 10(c) (650 mg, 1.36 mmol) was dissolved in $CH_2Cl_2$ (45 mL) and treated with 4.0 M HCl in dioxane (6.8 mL) for 2 h. The intermediate HCl salt (510 mg, 100%, MS (ES) m/e 376.2 [m+H]$^+$) was obtained by filtration of the resulting suspension, which was dissolved in 0.95 N NaOH solution (8.2 mL, 7.8 mmol) in EtOH (20 mL) and stirred for 18 h. The mixture was concentrated and filtered to give sodium salt of the titled compound (25 mg). MS (ES) m/e 348.2 [m+H]$^+$. Anal. Calcd. for $C_{17}H_{24}N_5O_3$Na.3.7 $H_2O$: C, 46.83; H, 7.26; N, 16.06; Found C, 47.02; H, 6.56; N, 15.61.

EXAMPLE 11

4-[[[4-(1-Piperazinyl)-3-chlorophenyl]amino]carbonyl]-1-piperdineacetic acid bis(trifluoroacetate)

a) 3-Chloro-4-(4-t-butoxycarbonyl-1-piperazinyl)nitrobenzene 44a

A solution of t-butyl 1-piperazinecarboxylate 38 (1.0 g., 5.37 mmole), 3-chloro-4-fluoronitrobenzene (0.94 g., 5.37 mmole) and diisopropylethylamine (0.70 g., 5.4 mmole) in DMSO (30 mL.) was heated 16 hours at 100°, cooled to r.t. and poured into ice water (300 mL.). The suspension was extracted with ethyl acetate (2×60 mL.). The combined organic layers were washed with water (3×40 mL.), dried over $Na_2SO_4$ and evaporated to dryness to give an orange solid which was recrystallized twice from methanol to give the title compound, 1.2 g. MS (M+H)$^+$ 342.0 b) 3-Chloro-4-(4-t-butoxycarbonyl-1-piperazinyl)aniline 45a

A suspension of the compound of Example 11(a) (0.34 g., 1.0 mmole) in ethanol (50 mL.) containing 10% Pd on C (0.2 g.) was hydrogenated at 40 psi at r.t. After 40 minutes, the mixture was filtered and evaporated to dryness to give the title compound, 0.31 g. MS (M+H)$^+$ 312.2 c) Ethyl 4-[[[4-(4-t-butoxycarbonyl)-1-piperazinyl)-3-chlorophenyl]amino]carbonyl]-1-piperidineacetate 46a A solution of ethyl 4-(chlorocarbonyl)-1-piperidineacetate hydrochloride 14 (0.27 g., 1.0 mmole) in methylene chloride (10 mL.) was added dropwise to a solution of the compound of Example 11(b) (0. 31 g., 1.0 mmole) and pyridine (0.16 g., 2.0 mmole) in methylene chloride (30 mL.). The solution was stirred 16 hours, extracted with 5% $Na_2CO_3$ (2×10 mL.) then with water (10 mL.), dried over $Na_2SO_4$ and evaporated to dryness. The residue was chromatographed (2.5% $CH_3OH/CH_2Cl_2$, silica) to give the title compound, 0.27 g. MS $(M+H)^+$ 509.4 d) 4-[[[4-(1-Piperazinyl)-3-chlorophenyl]amino]carbonyl]-1-piperdineacetic acid bis(trifluoroacetate)

A solution of the compound of Example 11(c) in a mixture of methylene chloride (35 mL.) and trifluoroacetic acid (10 mL.) was kept 16 hours at r.t. Solvents were removed and the residue redissolvled in a mixture of methanol (35 mL.), water (3.5 mL.) and 1 N NaOH (3.75 mL.). The solution was heated at 50° for 2 hours, cooled to r.t., quenched with trifluoroacetic acid (1.0 mL.) and evaporated to dryness to give a pale yellow solid which was purified by semi-preparative HPLC (YMC ODS-AQ, 10 μm, 120 Å, 50×250 mm.; 13% CH3CN/H2O, 0.1% TFA; 90 mL./min.) to give the title compound, 0.213 g. MS $(M+H)^+$ 381.2

EXAMPLE 12

4-[[[4-(1-piperazinyl)naphth-1-yl]amino]carbonyl]-1-piperidineacetic acid bis(trifluoroacetate)

a) 4-(4-t-butoxycarbonyl-1-piperazinyl)-1-nitronaphthlene 44b

Using the procedure of Example 11(a), except substituting 1-fluoro-4-nitronaphthalene 43b for 3-chloro-4-fluoronitrobenzene 43a, the title compound was prepared, 1.2 g. MS $(M+H)^+$ 358.2 b) 1-Amino-4-(4-t-butoxycarbonyl-1-piperazinyl)-naphthalene 45b

Using the procedure of Example 11(b), except substituting the compound of Example 12(a) for the compound of Example 11(a), the title compound was prepared, 0.65 g. MS $(M+H)^+$ 338.2 c) Ethyl 4-[[[4-(4-t-butoxycarbonyl-1-piperazinyl)naphth-1-yl]amino]carbonyl]-1-piperidineacetate 46b Using the procedure of Example 11(c), except substituting the compound of Example 12(b) for the compound of Example 11(b), the title compound was prepared, 0.45 g. MS $(M+H)^+$ 525.2 d) 4-[[[4-(1-piperazinyl)naphth-1-yl]amino]carbonyl]-1-piperidineacetic acid bis(trifluoroacetate)

Using the method of Example 11(d), except substituting the compound of Example 12(c) for the compound of Example 11(c), the title compound was prepared, 0.407 g. MS $(M+H)^+$ 397.2

EXAMPLE 13

4-[[[4-(1-Piperazinyl)-3-(trifluoromethyl)phenyl]amino]carbonyl]-1-piperidineacetic acid bis(trifluoroacetate)

a) 3-Trifluoromethyl-4-(4-t-butoxycarbonyl-1-piperazinyl)nitrobenzene 44c

Using the procedure of Example 11(a), except substituting 4-fluoro-3-(trifluoromethyl)nitrobenzene 43c for 3-chloro-4-fluoronitrobenzene 43a, the title compound was prepared, 0.95 g. MS $(M+H)^+$ 376.2 b) 3-Trifluoromethyl-4-(4-t-butoxycarbonyl-1-piperazinyl) aniline 45c

Using the procedure of Example 11(b), except substituting the compound of Example 13(a) for the compound of Example 11(a), the title compound was prepared, 0.69 g. MS $(M+H)^+$ 346.2 c) Ethyl 4-[[[4-(4-t-butoxycarbonyl)-1-piperazinyl)-3-(trifluoromethyl)-phenyl]amino]-carbonyl]-1-piperidineacetate 46c Using the procedure of Example 11(c), except substituting the compound of Example 13(b) for the compound of Example 1(b), the title compound was prepared, 0.45 g. MS $(M+H)^+$ 543.2 d) 4-[[[4-(1-Piperazinyl)-3-(trifluoromethyl)phenyl]amino]carbonyl]1-piperidineacetic acid bis(trifluoroacetate)

Using the method of Example 11(d), except substituting the compound of Example 13(c) for the compound of Example 11(c), the title compound was prepared, 0.302 g. MS $(M+H)^+$ 415.2

EXAMPLE 14

4-[[[4-(1-Piperazinyl)-2-(trifluoromethyl)phenyl]amino]carbonyl]-1-piperidineacetic acid bis(trifluoroacetate)

a) 2-Trifluoromethyl-4-(4-t-butoxycarbonyl-1-piperazinyl)nitrobenzene 44d

Using the procedure of Example 11(a), except substituting 4-fluoro-2-(trifluoromethyl)nitrobenzene 43d for 3-chloro-4-fluoronitrobenzene 43a, the title compound was prepared, 1.58 g. MS $(M+H)^+$ 376.2 b) 2-Trifluoromethyl-4-(4-t-butoxycarbonyl-1-piperazinyl) aniline 45d

Using the procedure of Example 11(b), except substituting the compound of Example 14(a) for the compound of Example 11(a), the title compound was prepared, 0.69 g. MS $(M+H)^+$ 346.2 c) Ethyl 4-[[[4-(4-t-butoxycarbonyl)-1-piperazinyl)-3-(trifluoromethyl)-phenyl]amino]-carbonyl]-1-piperidineacetate 46d Using the procedure of Example 11(c), except substituting the compound of Example 14(b) for the compound of Example 11(b), the title compound was prepared, 0.34 g. MS $(M+H)^+$ 543.2 d) 4-[[[4-(1-Piperazinyl)-3-(trifluoromethyl)phenyl]amino]carbonyl]-1-piperidineacetic acid bis(trifluoroacetate)

Using the method of Example 11(d), except substituting the compound of Example 14(c) for the compound of Example 11(c), the title compound was prepared, 0.172 g. MS $(M+H)^+$ 415.2

EXAMPLE 15

Preparation of 4-[N-(4,4'-Bipiperidinyl)aminol]carbonyl-1-piperidine acetic acid a) N-Boc-N'-benzylbipiperidine 48

Benzylbromide (2.19 ml, 18.5 mmol) was added to a mixture containing N-tert-butoxycarbonyl bipiperidine 47(3.3 g, 12.3 mmol) and triethylamine (2.57 ml, 18.5 mmol) in anhydrous DMF (10 ml), and the resulting mixture was stirred at RT for 4 hr. The reaction was concentrated on the rotavap (high vacuum). And the residue was dissolved in EtOAc, washed successively with $H_2O$, brine, dried ($MgSO_4$), concentrated and silica chromatography gave the title compound(2.8 g, 64%) as a white solid: MS (ES) m/e 359.2 $(M+H)^+$.

b) N-benzyl bipiperidine 47

Following the procedure of Example 3(b), except substituting the compound of 15(a) for Ethyl-4-[[[[4-(1-(tert-butoxycarbonyl)Piperazinyl]phenyl]amino]carbonyl]-1-piperidine acetate 16, the title compound (61%) as a white solid: (ES) m/e 259.2 (M+H)+.

c) N-benzyl-N'-nitrosobipiperidine 50

HCl (480 µl, 5.75 mmol, conc.) was added dropwise to a mixture containing the compound of 15(b) (1.34 g, 4.6 mmol) and acetic acid (4.6 ml, glacial) with cooling.Then it was heated to 25° C. and added a solution of potassium nitrite(1.17 g, 13.8 mmol) in $H_2O$ (3 ml) and kept at 25° C. for another 30 min. The product was extracted by $CH_2Cl_2$ and washed by $Na_2CO_3$, brine, after drying ($MgSO_4$) and concentrating gave 400 mg (30% yield) as a white solid: MS (ES) m/e 288.5 (M+H)+.

d) N-benzyl-N'-aminobipiperidine 51

To a refluxing LAH (3.5 mmol) in THF (7ml) was added dropwise a solution of the compound of Example 15(c) (400 mg, 1.4 mmol) in THF (10 ml) with stirring over 15 min. The resulting mixture was continued refluxing for 4 hr. $CH_3OH$ (a few drops) and NaOH (1M, 5 ml) was added, the product was extracted by THF and $Et_2O$, after drying ($MgSO_4$) and concentrating left 310 mg(81% yield) as a white solid: MS (ES) m/e 274.2 (M+H)+.

e) Ethyl 4-[N-benzylbipiperidinyl) amino]carbonyl-1-piperidine acetate 52

Following the procedure of Example 3(a), except substituting the compound of 15(d) for 4-[1-(tert-butoxycarbonyl) piperazinyl]aniline 3 the title compound (600 mg, 50%) as a white solid: (ES) m/e 471.4 (M+H)+.

f) Ethyl 4-[N-(4,4'-Bipiperidinyl) amino]carbonyl-1-piperidine acetate 53

A mixture of the compound of 15(e) (530 mg, 1.13 mmol) and Pearlman's catalyst (500 mg) in EtOH (100 ml) was subjected to hydrogenation at 50 Psi in a Parr apparatus at RT for 5 hr. The catalyst was removed by filtration and the filtrate was concentrated left 390 mg(91%) as a colorless foam: MS (ES) m/e 381.2 (M+H)+.

g) 4-[N-(4,4'-Bipiperidinyl)amino]carbonyl-1-piperidine acetic acid:

Following the procedure of Example 8(e), the compound of Example 15(d) was saponified to give the title compound as a white powder: MS (ES) m/e 353.5 (M+H)+. Anal. Calcd for $C_{18}H_{32}N_4O_3$·1.5 TFA.H2O: C, 46.58; H, 0.6.61; N, 10.35 Found: C, 46.59; H, 6.84; N, 10.36.

EXAMPLE 16

4-[4-(1-Piperazinyl)benzimidazol-2-yl]-1-piperidineacetic acid, tris(trifluoroacetate)

a) 5-[4-(t-butoxycarbonyl)-1-piperazinyl]-2-nitroaniline 55

A solution of t-butyl 1-piperazine carboxylate 38 (1.0 g., 5.4 mmole), 5-chloro-2-nitroaniline 54 (0.93 g., 5.4 mmole) and 1,4-diazabicyclo[2.2.2]octane (0.61 g., 54 mmole) in DMSO (10 mL.) was heated 16 hours under argon, cooled to r.t. and diluted with water (150 mL.) and extracted with ethyl acetate (3×50 mL.). The combined organic layers were washed with water (3×30 mL.) and dried over $Na_2SO_4$. Solvent was removed and the residue chromatographed (40% EtOAc/Hexane, silica) to give the title compound as a yellow solid, (0.5 g., 30%). MS (M+H)+ 323.

b) 4-[4-(t-butoxycarbonyl)-1-piperazinyl]-o-phenylenediamine 56

A solution of the compound of example 16(a) (0.30 g., 0.93 mmole) in ethanol (50 mL.) containing 10% Pd on carbon (0.10 g.) was hydrogenated at 40 psi for 40 minutes at r.t. The suspension was filtered and evaporated to give the title compound as a colorless solid, 0.27 g. MS (M+H)+ 293.2.

c) Mixture of ethyl 4-[[[4-[4-(t-butoxycarbonyl)-1-piperazinyl]-2-aminophenyl]-amino]carbonyl]-piperidin-4-yl-1-acetate,) ethyl 4-[[[5-[4-(t-butoxycarbonyl)-1-piperazinyl]-2-aminophenyl]amino]carbonyl]-piperidin-4-yl-1-acetate and N,N'-[4-(1-piperazinyl)-1,2-phenylene]bis-1-(carboethoxymethyl)-4-piperidinecarboxamide]57–59

A solution of ethyl 4-(chlorocarbonyl)-1-piperidineacetate hydrochloride 14 (0.25 g., 0.93 mmole) in methylene chloride (5.0 mL.) was added dropwise over 10 minutes to a solution of the Compound of Example 16b (0.27 g., 0.93 mmole) and diisopropylethylamine (0.26 g., 2.0 mmole) in methylene chloride (10 mL.). The mixture was stirred 16 hours, diluted with methylene chloride (35 mL.) and extracted with 5% $Na_2CO_3$. The organic layer was washed with water (3×20 mL.), dried over $Na_2SO_4$ and evaporated to give a pale yellow solid which was triturated with ether (30 mL.) to give the title mixture (0.17 g.). MS (M+H)+ 489.4, 674.5.

d) Mixture of ethyl 4-[5-[4-(t-butoxycarbonyl)-1-piperazinyl]benzimidazol-2-yl]-1-piperidineacetate and N,N'-[4-(1-piperazinyl)-1,2-phenylene]bis-[1-(carboethoxymethyl)-4-piperidinecarboxamide]60-61

A solution of the mixture of Example 16(c) in glacial acetic acid (30 mL.) was heated 16 hours at 65°, cooled to r.t. and evaportated to dryness to give the title mixture. MS (M+H)+ 471.4, 674.5.

e) 4-[5-(1-Piperazinyl)benzimidazol-2-yl]-1-piperidineacetic acid, tris(trifluoroacetate) and N,N'-[4-(1-piperazinyl)-1,2-phenylene]bis-[1-(carboxymethyl)-4-piperidinecarboxamide]-tetrakis(trifluoroacetate)

A solution of the mixture of Example 16(d) in a mixture of methylene chloride (20 mL.) and trifluoroacetic acid (5 mL.) was kept at r.t. for 16 hours and evaporated to dryness. A solution of the residue in a mixture of methanol (20 mL.), water (2.0 mL.) and 1.0 N NaOH (2.0 mL.) was heated for 2 hours at 50°, cooled to r.t. and treated with trifluoroacetic acid (0.8 mL.). Solvents were removed to give a pale yellow solid which was purified by semi-preparative HPLC (YMC ODS-AQ, 10 µm, 120 Å, 5×250 mm.; 5% $CH_3CN$/H2O, 0.1% TFA; 90 mL./min.) to give the title compound, 0.063 g. (eluting at 12.5 min.). MS (M+H)+ 344.2.

EXAMPLE 17

Preparation of N,N'-[4-(1-piperazinyl)-1,2-phenylenebis-[1-(carboxymethyl)-4-piperidinecarboxamide]tetrakis(trifluoroacetate)

(a) N,N'-[4-(1-piperazinyl)-1,2-phenylene]bis-[1-(carboxymethyl)-4-piperidinecarboxamide]tetrakis(trifluoroacetate)

The semi-preparative hplc purification of Example 16(e) also afforded the title compound, 0.040 g. (10.8 min.). MS (M+H)+ 531.2.

EXAMPLE 18

Preparation of 4-[[4-(1-Piperazinyl)phenyl]methylamino]carbonyl]-1-piperidineacetic acid a) 4-(1-N-trifluoroacetyl-4-piperazinyl)-N-formylaniline A solution of 4-(1-N-trifluoroacetyl-4-piperazinylaniline (1.2 g, 4 mmol) and Ethylformate (10 mL) was refluxed for 48 h. Reaction was concentrated. EtOAc was added and solution was washed consecutively with water, brine, dried over $MgSO_4$, filtered and concentrated to give the title compound (0.93 g, 77%). MS (ES) m/e 302 [M+H]+.

b) 4-(1-N-trifluoroacetyl-4-piperazinyl)-N-methylaniline

To a solution of compound of Example 18(a) (0.9 g, 3.1 mmol) in THF (15 mL) was added 2M $BH_3$dimethylsulfide complex (5 mL, 10 mmol). Reaction was refluxed for 2 h. 4M HCl in Dioxane (2 mL) and MeOH (2 mL) were added and reaction was refluxed for 1 h. Reaction was concentrated and title compound was crystallized from EtOAc/MeOH (0.54 g, 55%). MS (ES) m/e 361 [M+H]+.

c) Ethyl 4-chlorocarbonyl-1-piperidine acetate

A solution of ethyl-4-carboxy-1-piperidine acetate (0.44 g, 1.75 mmol) and thionyl chloride (0.2 mL, 3.9 mmol) in $CH_2Cl_2$ (3 mL) was stirred at RT for 4 h. Reaction was concentrated and carried on to the next step (0.47 g, Quant.)

d) Ethyl-4-[[[4-(4-Methyl-1-piperazinyl)phenyl]methylamino]carbonyl]-1-piperidine acetate To a stirred solution of compound of Example 18(c) (1.6 g, 1.7 mmol) in $CH_2Cl_2$ (3 mL) was added a solution of compound of Example 12(b) (0.46 g, 3 mmol) and $Et_3N$ (0.28 mL, 2 mmol) in $CH_2Cl_2$ (3 mL). Reaction was stirred for 18 h. Reaction was washed consecutively with water, 5% $NaHCO_3$, brine. Organic solution was concentrated to give the title compound (0.62 g, 75%). MS (ES) m/e 485 [M+H]+.

e) 4-[[[4-(1-Piperazinyl)phenyl]methylamino]carbonyl]-1-piperidine acetic acid

A solution of Ethyl4-[[[4-(1-Piperazinyl)phenyl]methylamino]carbonyl]-1-piperidine acetate (0.6 g, 0.23 mmol) in MeOH (3 mL) was treated with 1N NaOH (1.0 mL, 1.0 mmol). Solution was stirred at RT for 18 hr. Solution was concentrated and the residue was purified by prep HPLC (5% $CH_3CN$/0.1% TFA in water) to give the title compound (0.18 g, 20%). MS (ES) m/e 361 [M+H]+. $^1$HNMR (250 MHz, DMSO[d6]) δ 1.5–4.3 (m, 22H), 6.9–9.5 (m, 5H). Anal. ($C_{19}H_{28}N_4O$.3TFA.2.5$H_2O$) calcd: C, 39.83; H, 4.00; N, 6.98. found: C, 40.03; H, 4.18;N, 7.13.

EXAMPLE 19

Preparation of Sodium 4-[[[(1-piperizinyl)phenyl]carbonyl]amino]-1-piperidine acetate a)Sodium 4-[[[(1-piperizinyl)phenyl]carbonyl]amino]-1-piperidine acetate A solution of Sodium 4-[[[(1-benzyl-piperizinyl)phenyl]carbonyl]amino]-1-piperidine acetate (0.3 g, 0.98 mmol) and 10% Pd/C (0.1 g) in MeOH (40 mL) was hydrogenated (37 psi) for 5 hr. Solution was filtered through Celite and the filtrate was concentrated to givethe title compound (0.25 g, 85%). MS (ES) m/e 347 [M+H]+. $^1$HNMR (250 MHz, DMSO[d6]) δ 1.5–4.5 (m, 18H), 6.8–9.5 (m, 5H). Anal. ($C_{18}H_{25}N_4O_3$.0.75$CH_3OH$) calcd: C, 57.00; H, 7.01; N, 13.98. found: C, 57.19; H, 7.23; N, 14.10.

EXAMPLE 20

Preparation of 4-[N-[4-(1-piperazinyl)benzyl]-N-acetyl]amino-1-1-piperidineacetic acid a) 4-fluoro-methylbenzoate Thionyl chloride (16 mL, 0.22 mol) was added slowly to a solution of 4-fluorobenzoic acid (10 g, 71 mmol) in MeOH (200 mL). The reaction was stirred at RT for 18 h. Solution was evaporated to leave an oil (10.7 g, 97%). $^1$HNMR (250 MHz, DMSO[d6]) δ 3.8 (s, 3H), 7.0–8.1 (m, 4H).

b) 4-piperazinyl-methyl benzoate

A stirred solution of piperazine (2.6 g, 30.2 mmol) and methyl ester (1.93 g, 12.1 mmol) of Example 20(a) in DMSO (15 mL) was stirred at 65° C. for 18 h. Solution was cooled to RT. Reaction was treated with $NaHCO_3$ and extracted with EtOAc. The combined extracts were concentrated to afford the title compound (2.28 g, 84%). MS (ES) m/e 221 [M+H]+.

c) 4-[1'-(N-t-butyloxycarbonyl)-piperazinyl]-methyl benzoate $Boc_2O$ (2.5 g, 10.4 mmol) was added to a solution of the piperazine (2.28 g, 10.4 mmol) of Example 20(b) and $Et_3N$ (1.7 mL, 11 mmol) in $CH_3CN$ (40 mL). The reaction was stirred at RT for 18 h. Solution was filtered and the solid was washed with $CH_3CN$ to afford the title compound (1.88 g, 57%). MS (ES) m/e 321 [M+H]+.

d) 4-[1-(N-t-butyloxycarbonyl)-piperazinyl]-benzoic acid

The compound of Example 20(c) (1.88 g, 5.9 mmol) was dissolved in MeOH/THF (10 mL/100 mL) and treated with 1N NaOH (12 mL, 12 mmol). The solution was stirred at RT for 18 h. The solution was concentrated and the residue was taken up in water and AcOH was added dropwise until precipitation occurred. The solution was filtered and the solid was washed with water and dried in vacuo to give the title compound. (1.7 g, 94%). MS (ES) m/e 307 [M+H]+.

e) 4-[[[4-[4-(t-Butyloxycarbonyl)-1-piperazinyl]phenyl]carbonyl]amino]-1-benzyl-piperidine To a solution consisting of 4-amino-1-benzylpiperidine (1.1 mL, 4.8 mmol) in DMF (10 mL) was added $Et_3N$ until the pH was 9. To the resulting system was added consecutively HOBt (865 mg, 4.8 mmol), the compound of Example 20(d) (1.47 g, 4.5 mmol) and water soluble carbodiimide (1.0 g, 4.8 mmol). The resulting solution was stirred at RT for 18 h. The solution was concentrated and chromatographed using silica gel and $CH_2Cl_2$/MeOH (20/1). Desired fractions were concentrated to give the title compound. (1.84 g, 80%). MS (ES) m/e 479 [M+H]+ f) -[[[4-[4-(t-Butyloxycarbonyl)-1-piperazinyl]phenyl]carbonyl]amino]-1-piperidine A solution consisting of the compound of Example 20(e) (1.84 g, 3.8 mmol) and Pearlman's reagent (1.4 g) in MeOH (50 mL) was hydrogenated at 50 psi for 2.5 h. Reaction was filtered through Celite and the filtrate was concentrated to afford the title compound (1.5 g, 90%). MS (ES) m/e 389 [M+H]+.

g) t-Butyl-4-[[[4-[4-(t-Butyloxycarbonyl)-1-piperazinyl]phenyl]carbonyl]amino]-1-piperidine acetate A solution of compound of Example 20(f) (1.35 g, 3.5 mmol) and $Et_3N$ (0.727 mL, 4.0 mmol) in DMF (20 mL) was treated with t-butyl-bromo acetate (0.565 mL, 3.7 mmol). Reaction was stirred at RT for 18 h. Solution was concentrated to give title compound (1.65 g, 94%). MS (ES) m/e 503 [M+H]+.

h) t-Butyl-4-[[[4-[4-(t-Butyloxycarbonyl)-1-piperazinyl]phenyl]thiocarbonyl]amino]-1-piperidine acetate A stirred mixture of compound of Example 20(g) (0.86 g, 1.7 mmol) and Lawesson reagent (0.693 g, 1.7 mmol) in toluene (20 mL) was heated to 80° C. for 2 h. The solution was concentrated and chromatographed using silica gel and EtOAc/Hexane (1/1). Desired fractions were concentrated to give the title compound (0.56 g, 63%). MS (ES) 519 [M+H]+.

i) t-Butyl-4-[[4-[4-(t-Butyloxycarbonyl)-1-piperazinyl]benzyl]-amino]-1-piperidine acetate Sodium borohydride (0.894 mg, 24 mmol) was added to a cooled solution of compound of Example 20(h) (0.51 g, 0.98 mmol) and $NiCl_2$.6$H_2O$ (1.9 g, 8 mmol) in THF/MeOH (1/1). The reaction was stirred for 20 minutes. Solution was concentrated and residue was extracted with $CH_2Cl_2$. The combined extracts were concentrated to give the title compound (0.48 g, 85%) MS (ES) 489 [M+H]+.

j) t-Butyl-4-[[4-[4-(t-Butyloxycarbonyl)-1-piperazinyl]benzyl]-N-acetyl]amino-1-piperidine acetate Acetyl chloride (0.03 mL, 0.42 mmol) was added to a cooled solution of compound of Example 20(i) (0.205 g, 0.42 mmol) and $Et_3N$ (0.117 mL, 0.84 mmol) in $CH_2Cl_2$ (5 mL). The reaction was stirred at RT for 18 h. Solution was washed with 5% NaHCO$_3$ and H$_2$O. Organic layer was concentrated to give the title compound (0.23 g, 100%). MS (ES) 531 [M+H]$^+$.

k) 4-[N-[4-(-1-piperazinyl)]benzyl]-N-acetyl]amino-1-piperidine acetic acid

A solution of compound of Example 20(j) (0.23 g, 0.43 mmol) in CH$_2$Cl$_2$/TFA (1/1) was stirred at RT for 18 h. Reaction was concentrated and chromatographed using C-18 reversed-phase and CH$_3$CN (15% in water with 0.1% TFA). Desired fractions were concentrated to give the title compound (0.08 g, 50%). $^1$HNMR (250 MHz, DMSO[d6]) δ 1.5–4.5 (m, 24H), 6.9–7.3 (m, 4H). MS (ES) m/e 375 [M+H]$^+$. Anal. (C$_{20}$H$_{30}$N$_4$O$_3$.TFA.2.5 H$_2$O) calcd: C, 49.53; H, 6.80; N, 10.50. found: C, 49.83, H, 6.83, N, 10.46.

EXAMPLE 21

Preparation of 4-[[[4-(1-Piperazinyl)phenyl]amino] thiocarbonyl]-1-piperidine acetic acid 4-[[[4-(1-Piperazinyl)phenyl]amino]thiocarbonyl]-1-piperidine acetic acid a) Following the procedure of Example 20(k) except substituting compound of Example 20(h) for compound of Example 20(j), the title compound was prepared (0.040 g, 20%). $^1$HNMR (250 MHz, DMSO[d6]) δ 1.7–4.6 (m, 19H), 6.9–9.8 (m, 5H). ES (MS) m/e 363 [M+H]$^+$. Anal. (C$_{18}$H$_{26}$N$_4$O$_2$S.1.25TFA.2H$_2$O) calcd: C, 45.40; H, 5.78; N, 10.25. found: C, 45.48; H, 5.88; N, 10.37.

EXAMPLE 22

Preparation of 4-[[4-(1-piperazinyl)benzyl]amino]-1-piperidineacetic acid a 4-[[4-(1-piperazinyl)benzyl]amino-1-piperidine-acetic acid Following the procedure of Example 20(k) except substituting compound of Example 20(i) for compound of Example 20(j), the title compound was prepared (0.12 g, 86%). $^1$HNMR (250 MHz, DMSO[d6]) δ 1.5–4.2 (m, 21H), 7.0–9.1 (m, 6H). MS (ES) m/e 333 [M+H]$^+$. Anal. (C$_{18}$H$_{28}$N$_4$O$_2$.2H$_2$O.2TFA) calcd: C, 44.30; H, 5.74; N, 9.39. found: C, 44.60; H, 5.53; N, 9.32.

EXAMPLE 23

Preparation of 1-[[[4-(1-piperazinyl)phenyl]amino] carbonyl]-4-piperazineacetic acid a) 4-[4-trifluoracetyl)-1-piperazinyl]phenylisocyanate 5

4-[4-(trifluoroacetyl)-1-piperazinyl]aniline 4 (250 mg, 0.9 mmole) was dissolved in dioxane (5 ml) and TEA (125(1, 0.9 mmole). Trichloromethylchloroformate (110(1, 0.9 mmole) was added dropwise via syringe. Solid precipitated out upon addition, mixture stirred 30 min and was filtered to yield the title compound as a white solid (10 mg, 37%). MS (ES) m/e 300.2 [M+H]$^+$ b) methyl-1-[[[4-[1-(4-trifluoroacetyl)piperazinyl]phenyl] amino]carbonyl]-4-piperazine acetate 4

N-(carboethoxymethyl)piperazine 40 (280 mg, 16 mmole) in THF (5 ml) was added dropwise to the compound of example 23(a) dissolved in THF (10 ml) at room temperature. The solution stirred overnight was concentrated and chromatographed (2>3% MeOH/CH$_2$Cl$_2$, silica gel) to yield the title compound as a light brown solid (1.0 g, 26%). MS (ES) m/e 472.2 [M+H]$^+$ c) 1-[[[4-(1-piperazinyl)phenyl]amino]carbonyl]-4-piperazineacetic acid tris(trifluoroacetate) salt The compound of example 23(b) (700 mg, 1.5 mmole) was dissolved in MeOH (10 ml), 1N NaOH (4 ml) and H$_2$O (3 ml) and the solution stirred overnight. The MeOH was evaporated and aqueous solution brought to pH 6.5 with 1N HOAc. This solution was concentrated and residue purified by prep HPLC (YMC ODS-AQ, 50×250 mm, 10(m, 120 A, 220 nm, 80 ml/min, 0.1% TFA-2.5% CH$_3$CN/H$_2$O) to yield the title compound as a white solid (37 mg,7%). MS (ES) m/e 348.2 [M+H]$^+$

EXAMPLE 24

Preparation of 1-[[[4-(1-piperazinyl)phenyl]amino] carbonyl]-4-piperidine acetic acid a) 4-[(1-t-Butyloxycarbonyl)piperazine]-4-phenylisocyanate 42

To a stirred solution of) 4-[(1-t-Butyloxycarbonyl) piperazine]-4-aniline 3 (0.874 g, 3.15 mmol) in dioxane (4 mL), was added triethylamine (440 μL, 3.15 mmol) followed by a dropwise addition of diphosgene (0.623 g, 3.15 mmol). After a stirring of 2 h under argon, the triethylamine hydrochloride was filtered, and the filtrate was concentrated to afford the title compound as a white solid (0.56 g, 58.6%). MS (ESI) m/e 304.0 [M+H]$^+$. HPLC k' 8.2 (Ultrasphere® ODS, gradient, A:acetonitrile B:water-0.1% trifluoroacetic acid, 5–60% acetonitrile during 20 min; UV detection at 220 nm). IR (CH$_2$Cl$_2$ film on KBr crystal) 2261 cm$^{-1}$.

b) Ethyl-4-piperidine acetate hydrochloride 44

To a solution of ethyl-4-pyridine acetate (4.2 g, 2.5 mmol) in methanol (100 ml) was added PtO$_2$ (0.56 g, 2.5 mmol) and HCl (25 mL of 1N) under argon. The solution was hydrogenated under 50 psi for 4 h. The solution was filtered through celite, concentrated and triturated with ether to afford the title compound as a white solid (5.1 g, quantitative). MS (ESI) m/e 172 [M+H]$^+$. $^1$H NMR (400 MHz, CDCl$_3$) δ 6.25 (brs, 2H), 4.05 (q, 2H), 3.4 (m, 2H), 2.8 (m, 2H), 2.25 (d, 2H), 1.8 (d, 2H), 1.55 (d, 2H), 1.1 (t, 3H).

c) Ethyl-1-[[[4-(1-t-Butyloxycarbonyl)piperazinyl]phenyl] amino]carbonyl]-4-piperidine acetate 45

The compound of Example 24(a) (0.56 g, 1.85 mmol) was dissolved in dry THF (20 mL), treated with the compound of Example 24(b) (0.457 g, 2.2 mmol) and triethylamine (306 μL, 2.2 mmol). The solution was stirred under argon for 24 h. The reaction was concentrated and the residue was extracted with ethyl acetate and washed with water. The organic extract was dried (anhydrous Na$_2$SO$_4$), filtered, concentrated and chromatographed (silica gel, ethyl acetate), then recrystallized from ethyl acetate to afford the title compound as off white solid (0.56 g, 64%). MS (ESI) m/e 475.4 [M+H]$^+$. TLC R$_f$ 0.63 (silica gel, ethtyl acetate).

d) Ethyl-1-[[[4-(1-piperazinyl]phenyl]amino]carbonyl]-4-piperidine acetate

The compound of Example 24(c) (0.8 g, 1.69 mmol) in CH$_2$Cl$_2$ (10 ml) was added trifluoroacetic acid (10 ml) at RT and stirred for 1 h. The resulting solution was then concentrated to dryness on rotavap and evaporated with CH$_2$Cl$_2$ twice to afford the title compound. MS (ESI) m/e 375.4 [M+H]$^+$. HPLC k' 7.18 (Ultrasphere® ODS, gradient, A:acetonitrile B:water-0.1% trifluoroacetic acid, 5–60% acetonitrile during 20 min; UV detection at 220 nm).

e) 1-[[[4-(1-piperazinyl]phenyl]amino]carbonyl]-4-piperidine acetic acid

To a solution of the compound of Example 24(d) in ethanol (10 mL) was added a solution of 1N NaOH (12 ml) and was stirred at RT for 20 h. It was then concentrated, and the resulting oily residue was dissolved in H$_2$O, and the pH was adjusted to 7.08 by means of 50% acetic acid. The aqueous solution was purified on flash ODS column (step gradient, 4–6% acetonitrile/water. The fractions containing the pure compound were collected, concentrated and lyophilized to yield the title compound (430 mg, 73%) as a white powder. HPLC k' 5.2 (Ultrasphere® ODS, gradient, A:acetonitrile B:water-0.1% trifluoroacetic acid, 5–60% acetonitrile during 20 min; UV detection at 220 nm). MS (ESI) mle 347.2 [M+H]+; Anal. ($C_{18}H_{26}N_4O_4$·1.5 $H_2O$) calcd: C, 57.89; H, 7.83; N, 15.00. Found: C, 58.18; 7.79; N, 15.03. TLC $R_f$ 0.6 (silica gel, 1:1:1:1, ethtyl acetate,butanol, water, acetic acid).

EXAMPLE 25

Trans-4-[[[4-(1-piperazinyl)phenyl]amino]carbonyl]-1-hydroxy-1-cyclohexaneacetic acid (trifluoroacetate)

a) 4-Oxo-cyclohexanecarboxylic acid 47

A mixture of 2% $H_2SO_4$ and ethyl 4-oxo-cyclohexanoate 46 (10.0 g., 58.7 mmole) was stirred vigorously at 80° for 2 hours. The solution was cooled to r.t. and decanted. The supernatant was extracted with ether (3×150 mL.) and the combined organic layers dried over $Na_2SO_4$ and evaporated to dryness. The pale yellow residue was stirred with warm 30% ethyl acetate in hexane (200 mL.) and filtered. The title compound (3.5 g.) precipitated from the filtrate upon cooling. MS (M+H)+ 143.2 b) N-[4-[4-(t-butoxycarbonyl)-1-piperazinyl]phenyl]-4-oxo-cyclohexanecarboxamide 48

A solution of the compound of Example 25(a) (1.7 g., 12.0 mmole) in a mixture of methylene chloride (12.0 mL.) and dimethylformamide (1.9 mL.) was cooled to −40° under argon and a solution of thionyl chloride (1.43 g., 12.0 mmole) in methylene chloride (8 mL.) was added dropwise. The solution was stirred 30 minutes and a solution of 4-[4-(t-butoxycarbonyl)-1-piperazinyl]aniline 3 (3.3 g., 12.0 mmole) and triethylamine (2.4 g., 24.0 mmole) in methylene chloride (30 mL.) was added dropwise over one hour. The solution was allowed to stir at r.t. for two hours, diluted with methylene chloride (280 mL.), extracted with water (2×50 mL.), 5% $NaHCO_3$ (50 mL.) and water (50 mL.) and dried finally over $Na_2SO_4$. Removal of solvent gave a yellow solid purified by flash chromatography (3% $CH_3OH/CH_2Cl_2$, silica) to give the title compound, 2.0 g. MS (M+H)+ 402.2 c) Ethyl trans-4-[[[4-(4-t-butoxycarbonyl-1-piperazinyl)-phenyl]amino]carbonyl]-1-hydroxy-1-cyclohexaneacetate and ethyl cis-4-[[[4-(4-t-butoxycarbonyl-1-piperazinyl)-phenyl]amino]carbonyl]-1-hydroxy-1-cyclohexaneacetate 49

A solution of lithium bis(trimethylsilyl)amide (1.0 M in THF, 10.0 mL., 10 mmole) was added to anhydrous THF (80 mL.). The solution was cooled to −78° and a solution of ethyl acetate (0.88 g., 10 mmole) in THF (5.0 mL.) was added dropwise over five minutes. This solution was stirred 15 minutes and a solution of the compound of Example 25(b) (1.3 g., 3.24 mmole) in THF (65 mL.) was added dropwise over 15 minutes. The resulting mixture was stirred 25 minutes at −78°, quenched with glacial acid (1.0 mL.) and allowed to warm to r.t. Solvents were removed and the residue partitioned between ethyl acetate (300 mL.) and water (60 mL.). The organic layer was dried over $Na_2SO_4$ and evaporated to dryness to give a mixture of alcohols, 1.5 g. MS (M+H)+ 490.2 d) Trans-4-[[[4-(1-piperazinyl)phenyl]amino]carbonyl]-1-hydroxy-1-cyclohexaneacetic acid (trifluoroacetate) and cis-4-[[[4-(1-piperazinyl)phenyl]amino]carbonyl]-1-hydroxy-1-cyclohexaneacetic acid (trifluoroacetate)

A solution of the mixture of Example 25(c) in a mixture of methylene chloride (30 mL.) and trifluoroacetic acid (10 mL.) was kept overnight at 0°. Solvents were removed and the residue triturated with ether to give a colorless solid, which was dissolved in a mixture of methanol (50 mL.), water (5 mL.) and 1.0 N NaOH (5.0 mL.). This solution was heated at 50° for 2 hours, cooled to r.t. and treated with trifluoroacetic acid (1.5 mL.). Solvents were removed to give a pale yellow solid which was purified by semi-preparative HPLC (YMC ODS-AQ, 10 µm, 120 Å, 50×250 mm.; 12% $CH_3CN/H2O$, 0.1% TFA; 90 mL./min.) to give the title compound, 0.50 g. (eluting at 10.1 min.) and 0.44 g. (15.0 min.) respectively. MS (M+H)+ 362.2.

EXAMPLE 26 cis-4-[[[4-(1-piperazinyl)phenyl]amino]carbonyl]-1-hydroxy-1-cyclohexaneacetic acid (trifluoroacetate)

(a) cis-4-[[[4-(1-piperazinyl)phenyl]amino]carbonyl]-1-hydroxy-1-cyclohexaneacetic acid (trifluoroacetate)

The semi-preparative hplc purification of Example 25(d) also afforded the title compound, 0.44 g. (15.0 min.). MS (M+H)+ 362.2.

EXAMPLE 27

Preparation of 4-[[[4-Piperazinyl)phenyl]amino] carbonyl]-1-cyclohexanyl acetic acid a) Ethyl 4-trifluomethanesulfonylphenyl acetate 51

A solution containing ethyl 4-hydroxyphenyl acetate 50 (4.9 g, 27.2 mmol) and pyridine (6.6 ml, 82 mmol) in $CH_2Cl_2$(sure-seal, 17 ml) was added dropwise to a solution of trifluoromethanesulfonic anhydride (6.56 ml, 35.4 mmol) in $CH_2Cl_2$ (10 ml) with cooling under argon. After 4 h, the solvent was removed and the residual was tritilated with $Et_2O$-hexane, insoluble salt was removed by filtration and the filtrate was concentrated, after silica chromatography get 7.3 g (86% yield) as a light amber oil: MS (ES) m/e 313 (M+H)+.

b) Ethyl 4-carboxyphenyl acetate 52

A mixture of the compound of Example 27(a) (624 mg, 2 mmol), potassium acetate(784 mg, 8 mmol), palladium acetate(22.5 mg, 0.1 mmol) and 1,1'-Bis (diphenylphosphino)ferrocene (221.6 mg, 0.4 mmol) in DMSO(12 ml) was purged with carbon monoxide for 10 min. and then heated under CO balloon at 60° C. for 5 h. The reaction mixture was diluted with water, acidified with 0.5N hydrochloric acid and extracted with $CH_2Cl_2$. The organic layer was washed with water, dried ($Na_2SO_4$), and evaporated under vacuum The residue was chromatographed on solica gel and get 280 mg (67% yield) as an off white solid: MS (ES) m/e 224 (M+$NH_4$)+.

c) Ethyl 4-carboxycyclohexanylacetate 53

A mixture of the compound of 27(b) (1.1 g, 5.3 mmol) and platinum(IV) oxide (602 mg, 2.65 mmol) in acetic acid (60 ml) was hydrogenated at 50 psi in a Parr apparatus at RT for 5.5 hr. The reaction mixture was purged with argon, filtered and concentrated gave the title compound (1.01 g, 89%) as an clear oil: MS (ES) m/e 215.0 (M+H)+.

d) Ethyl-4-[[[[4-(1-(tert-butoxycarbonyl)Piperazinyl] phenyl]amino]carbonyl]-1-cyclohexanyl acetate 54

Following the procedure of Example 3(a), except substituting the compound of Example 27(c) for Ethyl 4-carboxypiperidinyl acetate 8, the title compound (1.9 g, 85.5%) as a pale yellow solid: (ES) m/e 474 (M+H)+.

e) Ethyl-4-[[[4-Piperazinyl]phenyl]amino]carbonyl]-1-cyclohexanyl acetate:

Following the procedure of Example 3(b), except substituting the compound of Example 27(d) for Ethyl-4-[[[[4-(1-(tert-butoxycarbonyl)Piperazinyl]phenyl]amino]carbonyl]-1-piperidine acetate 16, the title compound (71%) as a white solid: (ES) m/e 374 (M+H)+.

61 f) 4-[[[4-Piperazinyl)phenyl]amino]carbonyl]-1-cyclohexanyl acetic acid

Following the procedure of Example 8(e), the compound of Example 27(e) was saponified gave the title compound as a white powder: MS (ES) m/e 346.2 (M+H)+. Anal. Calcd for $C_{19}H_{27}N_3O_3$·1 HCl·0.33 $H_2O$: C, 58.83; H, 7.45; N, 10.83 Found: C, 59.10; H, 7.56; N, 10.81.

EXAMPLE 28

Preparation of 4-[[[4-(1-Piperazinyl)phenyl]amino]carbonyl]-1-piperidine propionic acid a) 4-(1-N-trifluoroacetyl-4-piperazinyl)nitrophenol Trifluoroacetic anhydride (7.5 mL, 48.5 mmol) was added to a cooled solution of 4-piperazinylnitrophenol (10 g, 48.3 mmol) and $Et_3N$ (13.5 mL, 96 mmol) in $CH_2Cl_2$ (100 mL). Reaction was stirred at RT for 1 h. Solution was washed consecutively with 5% $NaHCO_3$, $H_2O$, 5% citric acid and $H_2O$. The organic layer was concentrated. The crude was purified by flash chromatography (silica gel, EtOAc/Hexane (1/1) to yield the title compound (12.1 g, 83%). MS (ES) m/e 304 [M+H]+.

b) 4-(1-N-trifluoroacetyl-4-piperazinyl)aniline

To a solution of 4-(1-N-trifluoroacetyl-4-piperazinyl)nitrophenol (2.0 g, 6.6 mmol) in DMF/MeOH (20 mL/30 mL) was added 10% Pd/C (0.8 g). Solution was hydrogenated (45 psi) for 2 hr. Solution was filtered through Celite and the filtrate was concentrated to give the title compound (1.9 g, 100%). MS (ES) m/e 274 [M+H]+.

a) 4-[[[4-(1-N-trifluoroacetyl-4-Piperazinyl)phenyl]amino]carbonyl]-1-N-t-butyloxycarbonylpiperidine A mixture of 4-(1-N-trifluoroacetyl-4-piperazinyl)aniline (3.0 g, 9.9 mmol), Et3N (2.2 mL, 19 mmol), HOBt (1.5 g, 9.9 mmol), 1-t-butyloxycarbonyl- 4-carboxypiperidine (2.3 g, 9.9 mmol) and EDC (1.9 g, 9.9 mmol) in DMF (15 mL) was stirred at RT for 18 hr. Solution was concentrated and the residue was dissolved in EtOAc. EtOAc was washed with: H2O, 5% citric acid (2x), water, 5% NaHCO3 (2x), water and brine. EtOAc was concentrated to givethe title compound (4.35 g, 91%). MS (ES) m/e 485 [M+H]+.

b) 4-[[[4-(1-N-trifluoroacetyl-4-piperazinyl)phenyl]amino]carbonyl]-1-piperidine 4-[[[4-(1-N-trifluoroacetyl-4-Piperazinyl)phenyl]amino]carbonyl]-1-N-t-butyloxycarbonylpiperidine (2.0 g, 4.1 mmol) was treated with 4M Hcl (30 mL) for 1 hr. $Et_2O$ (100 mL) was added. Filtration gave the title compound (1.97 g, 100%). MS (ES) m/e 385 [M+H]+.

c) Methyl-4-[[[4-(1-N-trifluoroacetyl-4-piperazinyl)phenyl]amino]carbonyl]-1-piperidine acetate To a solution of 4-[[[4-(1-N-trifluoroacetyl-4-piperazinyl)phenyl]amino]carbonyl]-1-piperidine (0.90 g, 2.1 mmol) and Et3N (0.75 mL, 4.5 mmol) in DMF (5 mL) was added Methylbromoacetate (0.165 mL, 2.3 mmol). Solution was stirred at RT for 18 hr. Solution was concentrated and residue was taken up in EtOAc. EtOAc was washed successively with 5% citric acid (2x), water, 5% NaHCO3 (2x) and water. EtOAc was concentrated to give the title compound (0.200 g, 20%). MS (ES) m/e 473 [M+H]+.

d) 4-[[[4-(1-Piperazinyl)phenyl]amino]carbonyl]-1-piperidine propionic acid

Methyl-4-[[[4-(1-N-trifluoroacetyl-4-piperazinyl)phenyl]amino]carbonyl]-1-piperidine acetate (1.1 g, 2.1 mmol) was treated with 1N NaOH (4.5 mL, 4.5 mmol). Solution was stirred at RT for 18 hr. Solution was concentrated and chromatographed (C-18, 4% $CH_3CN$, 0.1% H2O) to givethe title compound (0.294 g, 39%). $^1$HNMR (250 MHz, DMSO [d6]) δ 1.5–4.0 (m, 20H), 6.8–9.7 (m, 5H). MS (ES) m/e 361 [M+H]+. Anal. ($C_{19}H_{28}N_4O_3$·3.5TFA·1.5$H_2O$) calcd: C, 39.70; H, 4.42; N, 7.12. found: C, 39.49; H, 4.29; N, 7.01.

EXAMPLE 29

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

EXAMPLE 30

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

EXAMPLE 31

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound of the formula:

$$R^1-N\underset{\phantom{X}}{\overset{\phantom{X}}{\bigcirc}}-A^3\underset{\|}{\overset{\phantom{X}}{-}}D-X-A^1\underset{\|}{\overset{\phantom{X}}{-}}\underset{\phantom{X}}{\overset{\phantom{X}}{\bigcirc}}-A^2-Q-\underset{\phantom{X}}{\overset{Z}{\underset{|}{C}}}-(CH_2)_{\overline{n}}-CO_2R^2$$

wherein:

$R^1$ is hydrogen or $C_{1-4}$alkyl;

D is

[phenylene group with Y and $Y^1$ substituents]

$A^1$ is CH;

$A^2$ is N;

$A^3$ is N;

Y and $Y^1$ independently are hydrogen, $C_{1-6}$alkyl, halogen or $CF_3$;

X is $NR^2C(O)$;

Q is a single bond;

Z is hydrogen;

n is 0 or 1; and each R² independently is H or C$_{1-4}$alkyl;

or a pharmaceutically acceptable salt thereof.

2. A compound according to claim 1 which is 4-[[[4-(1-piperazinyl)phenyl]amino]carbonyl]-1-piperidineacetic acid or a pharmaceutically acceptable salt thereof.

3. A compound according to claim 1 which is:

4-[[[4-(4-methyl-1-piperazinyl)phenyl]amino]carbonyl]-1-piperidineacetic acid;

4-[[[4-(1-piperazinyl)-3-(trifluoromethyl)phenyl]amino]carbonyl]-1-piperidineacetic acid;

4-[[[4-(1-piperazinyl)-2-(trifluoromethyl)phenyl]amino]carbonyl]-1-piperidineacetic acid;

4-[[[4-(1-piperazinyl)-3-chlorophenyl]amino]carbonyl]-1-piperdineacetic acid; or 4-[[[4-(1-piperazinyl)phenyl]N-ethylamino]carbonyl]-1-piperidineacetic acid;

or a pharmaceutically accetable salt thereof.

4. A pharmaceutical composition comprising a compound according to claim 1 and a pharmaceutically acceptable carrier.

5. A method for effecting inhibition of platelet aggregation which comprises administering an effective amount of a compound according to claim 1.

6. A method for treating stroke or a transient ischemia attack or myocardial infarction which comprises administering an effective amount of a compound according to claim 1.

* * * * *